United States Patent
Matsuo et al.

(10) Patent No.: US 9,796,652 B2
(45) Date of Patent: Oct. 24, 2017

(54) METHOD FOR MANUFACTURING (METH) ACRYLIC ACID ESTER AND METHOD FOR MANUFACTURING AROMATIC CARBOXYLIC ACID ESTER

(71) Applicant: MITSUBISHI RAYON CO., LTD., Chiyoda-ku (JP)

(72) Inventors: Takeshi Matsuo, Otake (JP); Naoshi Murata, Otake (JP); Hiroyuki Mori, Otake (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 15/308,232

(22) PCT Filed: May 27, 2015

(86) PCT No.: PCT/JP2015/065168
§ 371 (c)(1),
(2) Date: Nov. 1, 2016

(87) PCT Pub. No.: WO2015/190286
PCT Pub. Date: Dec. 17, 2015

(65) Prior Publication Data
US 2017/0050912 A1  Feb. 23, 2017

(30) Foreign Application Priority Data
Jun. 12, 2014 (JP) ................. 2014-121445
Jun. 12, 2014 (JP) ................. 2014-121446

(51) Int. Cl.
C07C 67/10 (2006.01)
C07C 67/11 (2006.01)

(52) U.S. Cl.
CPC .............. *C07C 67/10* (2013.01); *C07C 67/11* (2013.01)

(58) Field of Classification Search
CPC .................................................. C07C 67/02
See application file for complete search history.

(56) References Cited

U.S. PATENT DOCUMENTS

| | | | |
|---|---|---|---|
| 2,458,421 A | 1/1949 | Reynolds et al. | |
| 4,739,097 A * | 4/1988 | Sander | C07D 317/46 558/400 |
| 4,792,620 A * | 12/1988 | Paulik | B01J 31/0231 560/232 |
| 2011/0137072 A1 | 6/2011 | Ansai et al. | |
| 2014/0005435 A1 | 1/2014 | Ansai et al. | |

FOREIGN PATENT DOCUMENTS

| | | |
|---|---|---|
| JP | 62-132840 A | 6/1987 |
| JP | 2000-191590 A | 7/2000 |
| JP | 2002-3444 A | 1/2002 |
| JP | 2007-246503 A | 9/2007 |
| JP | 2011-105667 | 6/2011 |
| WO | WO 2010/016493 A1 | 2/2010 |
| WO | WO 2014/024207 A1 | 2/2014 |

OTHER PUBLICATIONS

Norskov et al, Nature Chemistry, Towards the Computational Design of Solid Catalysts, 2009, 1, pp. 37-46.*
International Search Report dated Aug. 25, 2015 in PCT/JP2015/065168 filed May 27, 2015.
Allen R. Banks, et al., "A Convenient Synthesis of Methacrylates" Journal of Organic Chemistry, vol. 42, No. 24, 1977, pp. 3964-3967.
Extended European Search Report dated Apr. 26, 2017 in Patent Application No. 15806000.4.

* cited by examiner

*Primary Examiner* — Paul A Zucker
(74) *Attorney, Agent, or Firm* — Oblon, McClelland, Maier & Neustadt, L.L.P.

(57) ABSTRACT

Provided is a method capable of efficiently manufacturing (meth)acrylic acid esters and aromatic carboxylic acid esters. This (meth)acrylic acid ester manufacturing method reacts a (meth)acrylic anhydride with a carbonate compound. For this aromatic carboxylic acid ester manufacturing method, which reacts a carboxylic anhydride with an aromatic carbonate in the presence of a catalyst, the catalyst is at least one kind selected from a set consisting of basic nitrogen-containing organic compounds, Group 1 metal compounds, and Group 2 metal compounds.

14 Claims, 1 Drawing Sheet

[Fig.1]
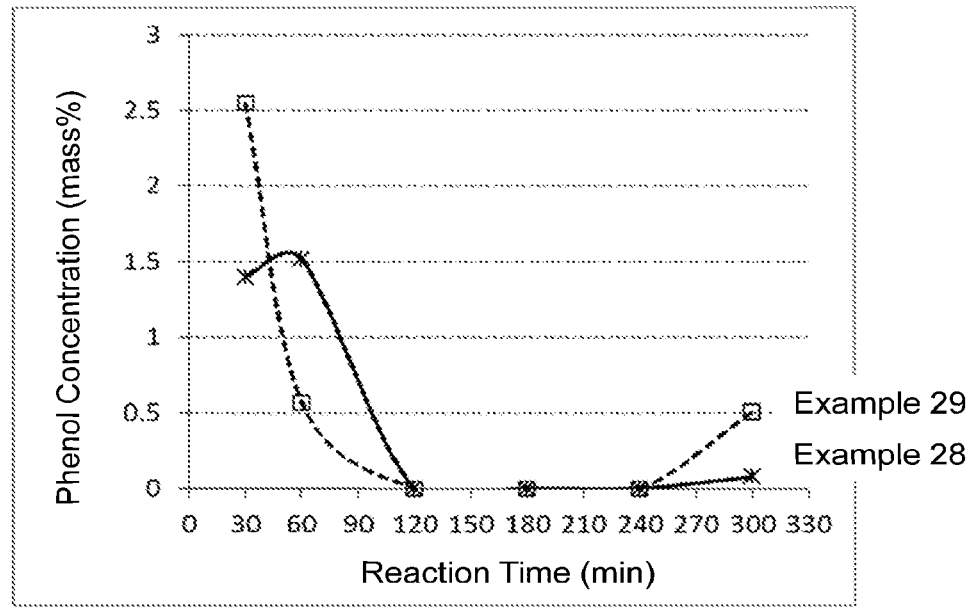
[Fig.2]
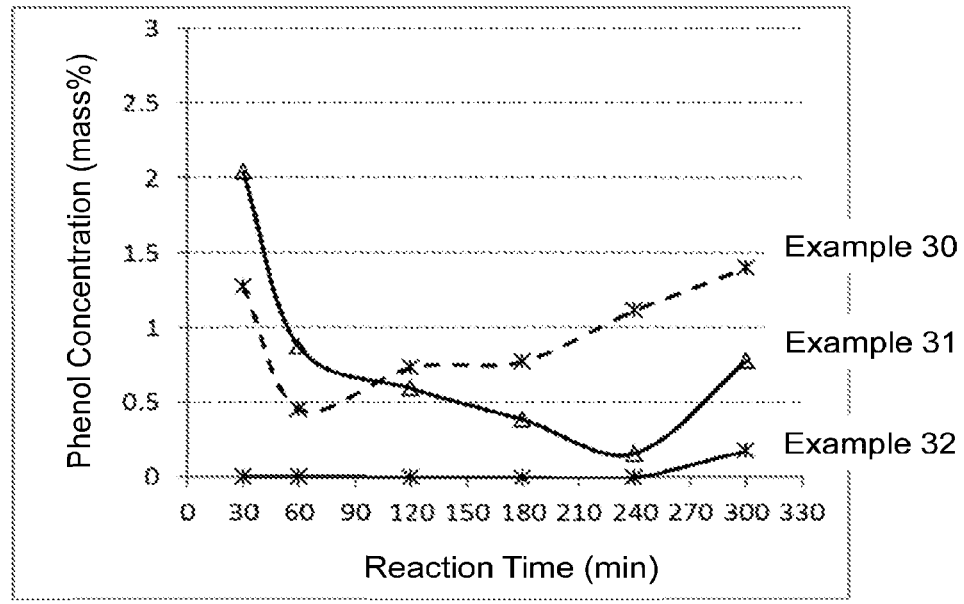

METHOD FOR MANUFACTURING (METH) ACRYLIC ACID ESTER AND METHOD FOR MANUFACTURING AROMATIC CARBOXYLIC ACID ESTER

TECHNICAL FIELD

The present invention relates to a method for manufacturing (meth) acrylic esters and a method for manufacturing aromatic carboxylic acid esters.

BACKGROUND ART

To manufacture (meth) acrylic acid esters, Patent Literature 1 discloses a method for conducting dehydration reactions on (meth) acrylic acid and alcohol in the presence of an acidic catalyst. Patent Literature 2 discloses a method for conducting transesterification on alcohol and a lower alkyl ester of (meth) acrylic acid. Non-Patent Literature 1 discloses a method for reacting (meth) acrylic acid chloride and alcohol in the presence of an amine.

Moreover, Patent Literature 3 discloses a method for conducting dehydration reactions on carboxylic acid and phenol in the presence of an acidic catalyst. Patent Literature 4 discloses a method for reacting esters of aromatic carboxylic acid and diphenyl carbonate.

CITATION LIST

Patent Literature

Patent Literature 1: JP S62-132840A
Patent Literature 2: JP2002-3444A
Patent Literature 3: JP2011-105667A
Patent Literature 4: JP2007-246503A

Non-Patent Literature

Non-Patent Literature 1: Journal of Organic Chemistry, 1977, 42, 3965

SUMMARY OF THE INVENTION

Problems to be Solved by the Invention

However, since the method described in Patent Literature 1 uses an acidic catalyst, quite a few byproducts are observed and the resulting (meth) acrylic acid ester is decomposed by the generated water. Accordingly, (meth) acrylic acid esters are not efficiently synthesized.

In the method described in Patent Literature 2, since transesterification reactions are equilibrium reactions, an excess amount of the lower alkyl ester of (meth) acrylic acid or alcohol as raw material is used. Accordingly, (meth) acrylic acid esters are not synthesized efficiently. In addition, the reactor is required to be equipped with a specific apparatus for efficiently removing the alcohol generated in the reactions.

When the method described in Non-Patent Literature 1 is employed, (meth) acrylic acid chloride used as raw material is expensive, a step for removing resulting amine hydrochloride causes a greater load on wastewater treatment, and so forth. Thus, the method is not preferable for industrial production.

Therefore, further improvement is desired for a method for manufacturing (meth) acrylic acid esters.

In addition, when the method in Patent Literature 3 is employed, the aromatic carboxylic acid ester is decomposed by the water generated in the reaction. Thus, it is difficult to set the equation of the equilibrium reaction in a forward direction for the production system to be favored. Accordingly, it is difficult to efficiently synthesize aromatic carboxylic acid esters.

When the method in Patent Literature 4 is employed, an excess amount of aromatic carboxylic acid ester relative to the amount of diphenyl carbonate is necessary. Accordingly, the produced amount of aromatic carboxylic acid ester per reaction volume is small.

Therefore, further improvement is desired for a method for manufacturing aromatic carboxylic acid esters.

The objective of the present invention is to provide methods for efficiently producing (meth) acrylic acid esters and aromatic carboxylic acid esters.

Solutions to the Problems

The aspects of the present invention are the following [1]~[15].

[1] A method for manufacturing a (meth) acrylic acid ester by reacting (meth) acrylic anhydride and a carbonate compound.

[2] The method for manufacturing a (meth)acrylic acid ester according to [1], in which the reaction is carried out using (meth) acrylic anhydride in a range of 0.1 mol~10 mol relative to 1 mol of a carbonate compound.

[3] The method for manufacturing a (meth) acrylic acid ester according to [1] or [2], in which the reaction is carried out in the presence of a carboxylic acid in a range of 0.001 mol~1.5 mol relative to 1 mol of a carbonate compound.

[4] The method for manufacturing a (meth) acrylic acid ester according to any of [1]~[3], in which the reaction is carried out in the presence of at least one type of catalyst selected from among nitrogenous base-containing organic compounds, Group I metal compounds, and Group II metal compounds.

[5] The method for manufacturing a (meth) acrylic acid ester according to [4], in which the catalyst is at least one type selected from among the compounds represented by formulas (5)~(7) below.

[chemical 1]

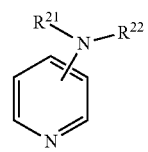

(5)

(In formula (5), the NR$^{21}$R$^{22}$ group is bonded to any of the 2-, 3-, and 4-positions of the pyridine ring. R$^{21}$R$^{22}$ are each independently hydrogen; a linear, branched-chain or ring C1~C30 alkyl group, which may have a substituent; a linear, branched-chain or ring C2~C30 alkenyl group, which may have a substituent; or a C6~C30 aryl group, which may have a substituent. $R^{21}R^{22}$ may be bonded to form a ring structure.)

[chemical 2]

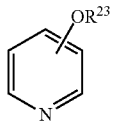

(6)

(In formula (6), the $OR^{23}$ group is bonded to any of the 2-, 3-, and 4-positions of the pyridine ring. $R^{23}$ is a linear, branched-chain or ring C1~C30 alkyl group, which may have a substituent; a linear, branched-chain or ring C2~C30 alkenyl group, which may have a substituent; or a C6~C30 aryl group, which may have a substituent.)

[chemical 3]

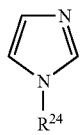

(7)

(In formula (7), $R^{24}$ is a linear, branched-chain or ring C1~C30 alkyl group, which may have a substituent, a linear, branched-chain or ring C2~C30 alkenyl group, which may have a substituent, or a C6~C30 aryl group, which may have a substituent.)

[6] The method for manufacturing a (meth) acrylic acid ester according to any of [1]~[5], in which the carbonate compound is diphenyl carbonate.

[7] The method for manufacturing a (meth) acrylic acid ester according to any of [1]~[6], in which phenothiazine is present in the reaction mixture as a polymerization inhibitor.

[8] The method for manufacturing a (meth) acrylic acid ester according to any of [1]~[7], in which part or all of the (meth) acrylic anhydride is added by sequentially or continuously to the mixture containing a carbonate compound.

[9] The method for manufacturing a (meth) acrylic acid ester according to any of [1]~[8], in which the reaction is carried out in the presence of a compound that contains a hydroxyl group in a range of 0.005 mass %~10 mass % relative to the entire reaction material.

[10] The method for manufacturing a (meth) acrylic acid ester according to any of [1]~[9], in which the reaction temperature is set to be in a range of 40° C.~200° C.

[11] A method for manufacturing an aromatic carboxylic acid ester by reacting a carboxylic anhydride and an aromatic carbonate in the presence of a catalyst, and the catalyst is at least one type selected from among nitrogenous base-containing organic compounds, Group I metal compounds, and Group II metal compounds.

[12] The method for manufacturing an aromatic carboxylic acid ester according to [11], in which the catalyst is at least one type selected from among the compounds represented by formulas (5)~(7) below.

[chemical 4]

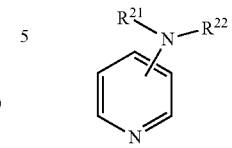

(5)

(In formula (5), the $NR^{21}R^{22}$ group is bonded to any of the 2-, 3-, and 4-positions of the pyridine ring. $R^{21}$ and $R^{22}$ are each independently hydrogen; a linear, branched-chain or ring C1~C30 alkyl group, which may have a substituent; a linear, branched-chain or ring C2~C30 alkenyl group, which may have a substituent; or a C6~C30 aryl group, which may have a substituent. $R^{21}R^{22}$ may be bonded to form a ring structure.)

[chemical 5]

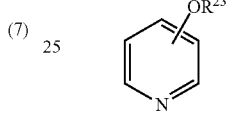

(6)

(In formula (6), the $OR^{23}$ group is bonded to any of the 2-, 3-, and 4-positions of the pyridine ring. $R^{23}$ is a linear, branched-chain or ring C1~C30 alkyl group, which may have a substituent; a linear, branched-chain or ring C2~C30 alkenyl group, which may have a substituent; or a C6~C30 aryl group, which may have a substituent.)

[chemical 6]

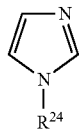

(7)

(In formula (7), $R^{24}$ is a linear, branched-chain or ring C1~C30 alkyl group, which may have a substituent; a linear, branched-chain or ring C2~C30 alkenyl group, which may have a substituent; or a C6~C30 aryl group, which may have a substituent.)

[13] The method for manufacturing an aromatic carboxylic acid ester according to [11] or [12], in which the aromatic carbonate is diphenyl carbonate.

[14] The method for manufacturing an aromatic carboxylic acid ester according to any of [11]~[13], in which the carboxylic anhydride is either acrylic anhydride or methacrylic anhydride.

[15] The method for manufacturing an aromatic carboxylic acid ester according to any of [11]~[14], in which the reaction temperature is set to be in a range of 40° C.~200° C.

Advantageous Effects of the Invention

By applying the aspects of the present invention, (meth) acrylic acid esters and aromatic carboxylic acid esters are efficiently manufactured.

BRIEF DESCRIPTION OF THE DRAWINGS

FIG. 1 is a graph showing the phenol concentration relative to reaction time in Examples 28 and 29; and FIG. 2 is a graph showing the phenol concentration relative to reaction time in Examples 30~32.

DETAILED DESCRIPTION OF PREFERRED EMBODIMENTS

First Embodiment

In a method for manufacturing a (meth) acrylic acid ester according to an embodiment of the present invention, (meth) acrylic anhydride and a carbonate compound are reacted. By using (meth) acrylic anhydride and a carbonate compound as raw materials in the method of the present embodiment, a (meth) acrylic acid ester is manufactured at high yield in a short period of time. In addition, since the amount of byproduct is less, productivity per batch is high, and the resulting amount of (meth)acrylic acid ester achieves a high ratio in proportion to the amount of raw material. Namely, (meth) acrylic acid esters are efficiently manufactured according to the present embodiment, while a simplified and industrially preferred manufacturing method is provided.

In the following, the manufacturing method of (meth) acrylic acid esters according to the present embodiment is provided in detail.

In the present application, (meth) acrylic acid means acrylic acid and/or methacrylic acid. Also, a (meth) acrylic acid ester means an acrylic acid ester and/or a methacrylic acid ester.

((Meth) Acrylic Anhydride)

(Meth) acrylic anhydride used in the present embodiment is not particularly limited to any type, and it may be acrylic anhydride, methacrylic anhydride or a mixture thereof. However, acrylic anhydride or methacrylic anhydride is preferred, and methacrylic anhydride is especially preferred.

The purity of (meth) acrylic anhydride used in the present embodiment is not specifically limited, but it is preferred to be 50 mass % or higher, more preferably 70 mass % or higher, even more preferably 83 mass % or higher, especially preferably 92 mass % or higher, and most preferably 96 mass % or higher. By using (meth) acrylic anhydride with a purity of 50 mass % or higher, a reduction in catalytic activity is suppressed, and an increase in production amount per reaction volume is achieved.

(Amount of (Meth) Acrylic Anhydride)

The amount of (meth) acrylic anhydride to be used in the present embodiment is not particularly limited, but it is preferred to be in a range of 0.1 mol~10 mol relative to 1 mol of the carbonate compound, as described later. When the amount of (meth) acrylic anhydride is set in a range of 0.1 mol~10 mol, the produced amount per reaction volume increases. Relative to 1 mol of the carbonate compound, the amount of (meth) acrylic anhydride is more preferred to be in a range of 0.33 mol~5 mol, even more preferably 0.6 mol~3 mol, especially preferably 0.83 mol~1.5 mol, and most preferably 0.95 mol~1.1 mol.

(Carbonate Compound)

A carbonate compound in the present embodiment indicates such a carbonate compound that has a carbonate group (—O—C(=O)—O—) bonded to a carbon atom in the molecule. The carbonate compound related to the present embodiment is not limited to any specific type, but is preferred to be a compound represented by formula (1) below.

[chemical 7]

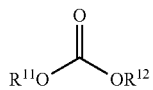

(1)

In formula (1), $R^{11}$ and $R^{12}$ are each independently a linear, branched-chain or ring C1~C30 alkyl group, which may have a substituent, a linear, branched-chain or ring C2~C30 alkenyl group, which may have a substituent; or a C6~C30 aryl group, which may have a sub stituent. $R^{11}$ and $R^{12}$ may be bonded to be in a ring form. In the present application, "may have a substituent" means containing at least one substituent of any type, for example, ester bond, amide bond, ether bond, sulfide bond, disulfide bond, urethane bond, amino group, nitro group, cyano group, thiol group, hydroxyl group, carboxyl group, ketone group, formyl group, acetal group, thioacetal group, sulfonyl group, halogen, silicon, phosphorous and the like.

Examples of a compound represented by formula (1) above are ethyl methyl carbonate, methyl phenyl carbonate, allyl methyl carbonate, dimethyl carbonate, diethyl carbonate, di(n-propyl) carbonate, diisopropyl carbonate, di(n-butyl) carbonate, di(tert-butyl) carbonate, dibenzyl carbonate, triphosgene, diphenyl carbonate, dinaphthyl carbonate, di(4-nitrophenyl) carbonate, di(o-tolyl) carbonate, ethylene carbonate, propylene carbonate, trimethylene carbonate, vinylene carbonate, cyclohexene carbonate, o-phenylene carbonate and the like.

A carbonate compound is preferred to be a compound represented by formula (2) or (3) below.

[chemical 8]

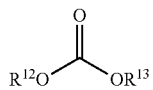

(2)

In formula (2), $R^{13}$ is a linear, branched-chain or ring C1~C30 alkyl group, which may have a substituent; a linear, branched-chain or ring C2~C30 alkenyl group, which may have a substituent; or a C6~C30 aryl group, which may have a substituent.

[chemical 9]

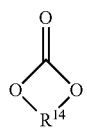

(3)

In formula (3), $R^{14}$ is a linear, branched-chain or ring C2~C30 alkylene group, which may have a substituent; a linear, branched-chain or ring C2~C30 alkenylene group, which may have a substituent; or a C6~C30 arylene group, which may have a substituent.

Examples of the compound represented by formula (2) are dimethyl carbonate, diethyl carbonate, di(n-propyl) carbonate, diisopropyl carbonate, di(n-butyl) carbonate, di(tert-butyl) carbonate, dibenzyl carbonate, triphosgene, diphenyl carbonate, dinaphthyl carbonate, di(4-nitrophenyl) carbonate, di(o-tolyl) carbonate, and the like.

Examples of the compound represented by formula (3) are ethylene carbonate, propylene carbonate, trimethylene carbonate, vinylene carbonate, cyclohexene carbonate, o-phenylene carbonate, and the like. These carbonate compounds may be used alone or in combination thereof.

Carbonate compounds are more preferred to be those represented by formula (4) below.

[chemical 10]

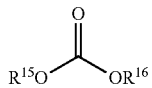

(4)

In formula (4), $R^{15}$ is a C6~C30 aryl group, which may have a substituent.

Examples of the compound represented by formula (4) are diphenyl carbonate, dinaphthyl carbonate, di(4-nitrophenyl) carbonate, di(o-tolyl) carbonate, and the like.

Among those listed above, diphenyl carbonate is especially preferred to suppress side reactions.

The molecular weight (number-average molecular weight) of the carbonate compound used in the present embodiment is not limited specifically, but it is preferred to be 90~100000. By setting the molecular weight of a carbonate compound at 90~100000, the carbonate compound will be mixed efficiently during reaction, and the reaction thereby progresses efficiently. The molecular weight (number-average molecular weight) of a carbonate compound is more preferred to be 90~50000, even more preferably 90~10000, especially preferably 90~3000, and most preferably 90~1000. Here, the molecular weight (number-average molecular weight) of a carbonate compound is determined by gel permeation chromatography (GPC).

(Purity of Carbonate Compound)

The purity of a carbonate compound in the present embodiment is not limited specifically, but it is preferred to be 50 mass % or higher, more preferably 70 mass % or higher, even more preferably 90 mass % or higher, especially preferably 95 mass % or higher, and most preferably 98 mass % or higher. Using a carbonate compound with a purity of 50 mass % or higher enables an increase in the produced amount of a (meth) acrylic acid ester per reaction volume.

(Catalyst)

It is an option to use a catalyst when (meth) acrylic anhydride and a carbonate compound are reacted in a reaction mixture. However, a catalyst is preferred to be used to enhance the reaction rate. The catalyst to be used is not limited to a specific type as long as a (meth) acrylic acid ester is efficiently produced. Considering the reaction rate, a catalyst is preferred to be at least a type selected from among nitrogenous base-containing organic compounds, Group I metal compounds and Group II metal compounds, which may be used alone or in combination thereof. A nitrogenous base-containing organic compound means a nitrogenous base is contained in the organic compound.

(Nitrogenous Base-Containing Organic Compound)

A nitrogenous base-containing organic compound is not particularly limited to any type; for example, primary, secondary and tertiary amine compounds, aromatic amine compounds, imine compounds, nitrogen-containing heterocyclic compounds and the like may be used.

A nitrogenous base-containing organic compound may have multiple nitrogen atoms in its molecule. Examples of a nitrogenous base-containing organic compound having multiple nitrogen atoms are those containing two moieties selected from among primary, secondary and tertiary amine moieties, an imine moiety, and a nitrogen-containing heterocyclic moiety. In the present application, a nitrogenous base-containing organic compound that contains a nitrogen-containing heterocyclic moiety and a nitrogenous base-containing moiety is referred to as a nitrogen-containing heterocyclic compound; a nitrogenous base-containing organic compound that contains an imine moiety and a primary, secondary or tertiary amine moiety is referred to as an imine compound; a nitrogenous base-containing organic compound that contains a tertiary amine moiety and a primary or secondary amine moiety is referred to as a tertiary amine compound; and a nitrogenous base-containing organic compound that contains a secondary amine moiety and a primary amine moiety is referred to as a secondary amine compound.

A nitrogenous base-containing organic compound is preferred to be a nitrogen-containing heterocyclic compound or an imine compound, more preferably a nitrogen-containing heterocyclic compound.

A nitrogen-containing heterocyclic compound contains the following, for example, in its molecule: pyrrole ring, pyridine ring, azepine ring, imidazole ring, pyrazole ring, oxazole ring, imidazoline ring, pyrazine ring, indole ring, isoindole ring, benzimidazole ring, purine ring, quinoline ring, isoquinoline ring, quinoxaline ring, cinnoline ring, pteridine ring, acridine ring, carbazole ring, porphyrin ring, chlorin ring, choline ring, diazabicycloundecene ring, diazabicyclononene ring or the like.

Among them, the molecule of a nitrogen-containing heterocyclic compound is preferred to contain at least one selected from among a pyrrole ring, pyridine ring, azepine ring, imidazole ring, pyrazole ring, oxazole ring, imidazoline ring, pyrazine ring, indole ring, benzimidazole ring, quinoline ring, diazabicycloundecene ring, and diazabicyclononene ring.

The molecule of a nitrogen-containing heterocyclic compound is more preferred to contain at least one selected from among a pyrrole ring, pyridine ring, imidazole ring, pyrazole ring, imidazoline ring, pyrazine ring, benzimidazole ring, diazabicycloundecene ring, and diazabicyclononene ring. Furthermore, the molecule of a nitrogen-containing heterocyclic compound is even more preferred to contain a ring selected from among a pyridine ring, imidazole ring, diazabicycloundecene ring and diazabicyclononene ring.

Examples of a nitrogen-containing heterocyclic compound having a pyridine ring are pyridine, 2-methylpyridine, 2-ethylpyridine, 2-phenylpyridine, 2-cyanopyridine, 2-hydroxypyridine, 2-(aminomethyl)pyridine, 2-aminopyridine, 2-(methylamino)pyridine, 2-dimethylaminopyridine, 3-methylpyridine, 3-ethylpyridine, 3-phenylpyridine, 3-cyanopyridine, 3-hydroxypyridine, 3-(aminomethyl)pyridine, 3-(methylamino)pyridine, 3-aminopyridine, 4-methylpyridine, 4-ethylpyridine, 4-tert-butylpyridine, 4-phenylpyridine, 4-cyanopyridine, 4-hydroxypyridine, 4-(aminomethyl)pyridine, 4-aminopyridine, 4-(methylamino)pyridine, 4-dimethylaminopyridine, 4-diethylaminopyridine, 4-anilinopyridine, 4-pyrrolidinopyridine, 4-(4-pyridyl)morpholine, 4-(4-aminopiperidino)pyridine, 4-methoxypyridine, 4-ethoxypyridine, 4-phenoxypyridine, 2,6-dimethylpyridine, 2,6-diaminopyridine, 3,5-dimethylpyridine, 2,2'-bipyridine, 4,4'-bipyridine, 4,4'-dimethyl-2,2'-bipyridine, and the like.

Examples of a nitrogen-containing heterocyclic compound having an imidazole ring are imidazole, 1-methylimidazole, 1-ethylimidazole, 1-propylimidazole, 1-isopropylimidazole, 1-butylimidazole, 1-phenylimidazole, 2-methylimidazole, 2-ethylimidazole, 2-propylimidazole, 2-isopropylimidazole, 2-butylimidazole, 2-phenylimidazole, 2-aminoimidazole, 2-formylimidazole, 4-methylimidazole, 4-ethylimidazole, 5-methylimidazole, 5-ethylimidazole, 1,2-dimethylimidazole, and the like.

Examples of a nitrogen-containing heterocyclic compound having a diazabicycloundecene ring are 1,8-diazabicyclo[5.4.0]-7-undecene, and the like.

Examples of a nitrogen-containing heterocyclic compound having a diazabicyclononene ring are 1,5-diazabicyclo[4.3.0]-5-nonene, and the like.

In addition, when the reaction rate is considered, a nitrogen-containing heterocyclic compound is preferred to be a compound represented in formula (5)~(7) below.

[chemical 11]

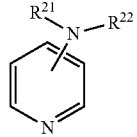

(5)

In formula (5), the $NR^{21}R^{22}$ group is bonded to any of the 2-, 3-, and 4-positions of the pyridine ring. $R^{21}$ and $R^{22}$ are each independently hydrogen; a linear, branched-chain or ring C1~C30 alkyl group, which may have a substituent; a linear, branched-chain or ring C2~C30 alkenyl group, which may have a substituent; or a C6~C30 aryl group, which may have a substituent. $R^{21}R^{22}$ may be bonded to form a ring structure.

[chemical 12]

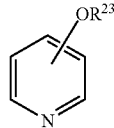

(6)

In formula (6), the $OR^{23}$ group is bonded to any of the 2-, 3-, and 4-positions of the pyridine ring. $R^{23}$ is a linear, branched-chain or ring C1~C30 alkyl group, which may have a substituent; a linear, branched-chain or ring C2~C30 alkenyl group, which may have a substituent; or a C6~C30 aryl group, which may have a substituent.

[chemical 13]

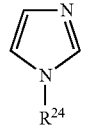

(7)

In formula (7), $R^{24}$ is a linear, branched-chain or ring C1~C30 alkyl group, which may have a substituent; a linear, branched-chain or ring C2~C30 alkenyl group, which may have a substituent, or a C6~C30 aryl group, which may have a substituent.

Examples of a compound represented by formula (5) above are 2-aminopyridine, 2-(methylamino)pyridine, 2-dimethylaminopyridine, 3-aminopyridine, 3-(methylamino) pyridine, 3-dimethylaminopyridine, 4-aminopyridine, 4-(methylamino)pyridine, 4-dimethylaminopyridine, 4-diethylaminopyridine, 4-anilinopyridine, 4-pyrrolidinopyridine, 4-(4-pyridyl)morpholine, 4-(4-aminopiperidino)pyridine, and the like.

Examples of a compound represented by formula (6) above are 2-methoxypyridine, 3-methoxypyridine, 4-methoxypyridine, 4-ethoxypyridine, 4-phenoxypyridine, and the like.

Examples of a compound represented by formula (7) above are 1-methylimidazole, 1-ethylimidazole, 1-propylimidazole, 1-isopropylimidazole, 1-butylimidazole, 1-phenylimidazole, and the like.

A nitrogen-containing heterocyclic compound is more preferred to be a compound represented in formula (8) below.

[chemical 14]

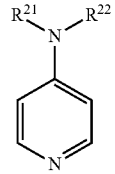

(8)

In formula (8), $R^{21}$ and $R^{22}$ are each independently hydrogen; a linear, branched-chain or ring C1~C30 alkyl group, which may have a substituent; a linear, branched-chain or ring C2~C30 alkenyl group, which may have a substituent; or a C6~C30 aryl group, which may have a substituent.

Examples of a compound represented by formula (8) above are 4-aminopyridine, 4-(methylamino)pyridine, 4-dimethylaminopyridine, 4-diethylaminopyridine, 4-anilino pyridine and the like.

A nitrogen-containing heterocyclic compound is most preferred to be 4-dimethylaminopyridine. Those nitrogen-containing heterocyclic compounds listed above may be used alone or in combination thereof.

(Group I Metal Compound)

The metal contained in a Group I metal compound is not limited to a specific metal, but lithium, sodium or potassium is preferred, more preferably lithium or sodium, because such a catalyst can increase the reaction rate.

Group I metal compounds are preferred to contain ligands. Examples of a ligand are acrylic acid ion, methacrylic acid ion, formalic acid ion, acetic acid ion, acetylacetonate ion, trifluoro-2,4-pentanedionate ion, phenoxy ion, methoxy ion, hydroxide ion, carbonate ion, bicarbonate ion and the like.

Ligands are preferred to be ions, more preferably ions consisting of organic molecules, even more preferably carboxylic acid or aromatic alkoxy ions. Especially preferred ligands are acrylic acid, methacrylic acid or phenoxy ions, and most preferably methacrylate or phenoxy ions.

Group I metal compounds having ionic ligands consisting of organic molecules are, for example, lithium acrylate, lithium methacrylate, lithium formate, lithium acetate, lithium phenoxide, lithium methoxide, sodium acrylate, sodium methacrylate, sodium formate, sodium acetate, sodium phenoxide, sodium methoxide, potassium acrylate, potassium methacrylate, potassium formate, potassium acetate, potassium phenoxide, potassium methoxide, and the like.

Among those listed above, the Group I metal compound is preferred to be lithium acrylate, lithium methacrylate, sodium acrylate, sodium methacrylate, potassium acrylate, potassium methacrylate, lithium phenoxide, sodium phenoxide, or potassium phenoxide.

In addition, the Group I metal compound is more preferred to be lithium acrylate, lithium methacrylate, sodium acrylate, sodium methacrylate, lithium phenoxide, or sodium phenoxide; even more preferably, lithium methacrylate, lithium phenoxide, sodium methacrylate, or sodium phenoxide. Those Group I metal compounds may be used alone or in combination thereof.

(Group II Metal Compound)

The metal contained in a Group II metal compound is not limited to a specific metal, but beryllium, magnesium or calcium is preferred, more preferably magnesium or calcium, even more preferably, magnesium, since such a catalyst can increase the reaction rate.

Group II metal compounds are preferred to contain ligands. Examples of a ligand are acrylic acid ion, methacrylic acid ion, formic acid ion, acetic acid ion, acetylacetonate ion, trifluoro-2,4-pentanedionate ion, phenoxy ion, methoxy ion, hydroxide ion, carbonate ion, bicarbonate ion, and the like.

Ligands are preferred to be ions, more preferably ions consisting of organic molecules, even more preferably carboxylate or aromatic alkoxy ions, especially preferably acrylate, methacrylate or phenoxy ions, and most preferably methacrylate or phenoxy ions.

Group II compounds having ionic ligands consisting of organic molecules are, for example, beryllium acrylate, beryllium methacrylate, beryllium formate, beryllium acetate, beryllium phenoxide, beryllium methoxide, magnesium acrylate, magnesium methacrylate, magnesium formate, magnesium acetate, magnesium phenoxide, magnesium methoxide, magnesium acetylacetonate, bis(trifluoro-2,4-pentanedionate)magnesium, calcium acrylate, calcium methacrylate, calcium formate, calcium acetate, calcium phenoxide, calcium methoxide, calcium acetylacetonate, bis(trifluoro-2,4-pentanedionate)calcium, and the like.

Among them, the Group II metal compound is preferred to be magnesium acrylate, magnesium methacrylate, calcium acrylate, calcium methacrylate, magnesium phenoxide, calcium phenoxide, magnesium acetylacetonate, or calcium acetylacetonate.

The Group II metal compound is more preferred to be magnesium acrylate, magnesium methacrylate, magnesium phenoxide, or magnesium acetylacetonate; even more preferably magnesium acrylate, magnesium methacrylate, or magnesium phenoxide; especially preferably magnesium methacrylate or magnesium phenoxide. Those Group II metal compounds may be used alone or in combination thereof.

(Amount of Catalyst)

The amount of catalyst used in the present embodiment is not particularly limited as long as a (meth) acrylic acid ester is efficiently produced. The amount is preferred to be in a range of 0.0001 mol~0.5 mol relative to 1 mol of a carbonate compound. When the amount is set to be at least 0.0001 mol relative to 1 mol of the carbonate compound, a decrease in catalytic activity caused by impurities is effectively suppressed. When the amount is set to be no greater than 0.5 mol relative to 1 mol of the carbonate compound, a decrease in productivity and purity in a resulting (meth) acrylic acid ester is efficiently prevented.

Relative to 1 mol of a carbonate compound, the amount of catalyst is more preferred to be in a range of 0.0003 mol~0.3 mol, even more preferably 0.0005 mol~0.2 mol, especially preferably 0.001 mol~0.15 mol, and most preferably 0.005 mol~0.07 mol.

The catalyst used in the present embodiment may or may not be dissolved in a reaction mixture; however, it is preferred to be dissolved. A catalyst dissolved in a reaction mixture is capable of increasing the reaction rate of producing a (meth)acrylic acid ester.

(Carboxylic Acid)

A (meth)acrylic anhydride and a carbonate compound may be reacted with or without a carboxylic acid; however, the reaction is preferred to be carried out in the presence of a carboxylic acid considering the reaction rate.

As a carboxylic acid to be present, its type is not limited specifically, but (meth)acrylic acid is preferred to suppress side reactions. Especially, acrylic acid is preferred when acrylic anhydride is used, and methacrylic acid is preferred when methacrylic anhydride is used.

When a carboxylic acid is added, the number of moles of the carboxylic acid is preferred to be in a range of 0.001 mol~1.5 mol relative to 1 mol of a carbonate compound. By setting the number of moles of a carboxylic acid to be 0.001 mol or greater relative to 1 mol of a carbonate compound, reaction progresses efficiently. By setting the number of moles of the carboxylic acid to be no greater than 1.5 mol relative to 1 mol of the carbonate compound, the produced amount per reaction volume is increased.

Relative to 1 mol of a carbonate compound, the amount of added carboxylic acid is preferred to be in a range of 0.005 mol~1 mol, more preferably 0.01 mol~0.7 mol, especially preferably 0.05 mol~0.55 mol, and most preferably 0.1 mol~0.3 mol.

The timing for a carboxylic acid to be present is not particularly limited; it may be present prior to reacting (meth)acrylic anhydride and a carbonate compound, or it may be present or added during the reaction.

(Solvent)

(Meth)acrylic anhydride and a carbonate compound may be reacted in a solvent. However, it is preferred not to use a solvent from a viewpoint of productivity. When a solvent is used, its type is not limited particularly, but it is preferred to be a C1~C25 organic compound. The solvent may contain one or more of the following: double bond, triple bond, amide bond, ether bond, sulfide bond, nitro group, cyano group, ketone group, halogen, silicon, phosphorous and the like. Also, the solvent may have a cyclic or aromatic ring structure. The amount of solvent is not specifically limited.

Examples of a solvent are benzene, toluene, xylene, n-hexane, cyclohexane, n-heptane, n-octane, n-nonane, n-decane, 1,4-dioxane, tetrahydrofuran, tetrahydropyran, anisole, methyl-tert-butyl ether, dibutyl ether, diphenyl ether, ethylene glycol monomethyl ether, ethylene glycol monoethyl ether, ethylene glycol mono-n-butyl ether, acetone, methyl ethyl ketone, methyl-n-butyl ketone, methyl isobutyl ketone, cyclohexanone, 2-methylcyclohexanone, dimethylformamide, dimethylacetamide and the like. They may be used alone or in combination thereof.

(Polymerization Inhibitor)

When (meth)acrylic anhydride and a carbonate compound are reacted in the present embodiment, the reaction is preferred to be carried out in the presence of a polymerization inhibitor.

Examples of a polymerization inhibitor are phenol-based polymerization inhibitors such as phenol, 1,4-benzenediol, 4-methoxyphenol, 2,6-di-tert-butylphenol, 2,4-di-tert-butylphenol, 2-tert-butyl-4,6-dimethylphenol, 2,6-di-tert-butyl-4-methylphenol, and 2,4,6-tri-tert-butylphenol; amine-based polymerization inhibitors such as N,N'-dialkylated-p-diphenylamine, N,N'-diphenyl-p-phenylenediamine, N,N'-di-2-naphthyl-p-phenylenediamine, N-phenyl-N'-(1,3-dimethylbutyl)-p-phenylenediamine, and phenothiazine; copper dithiocarbamate-based polymerization inhibitors such as metallic copper, copper sulfate, copper dimethyldithiocarbamate, copper diethyldithiocarbamate, and copper dibutyldithiocarbamate; N-oxyl based compounds such as 4-hydroxy-2,2,6,6-tetramethylpiperidine-N-oxyl (HO-TEMPO), 4-benzoyloxy-2,2,6,6-tetramethylpiperidine-N-oxyl (BTOX), and 4-acetoxy-2,2,6,6-tetramethylpiperidine-N-oxyl;

N-oxyl-based polymerization inhibitors represented by formula (9) below; and so on.

[chemical 15]

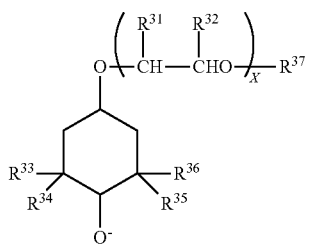

(9)

In formula (9) above, k=1~18. $R^{31}$ and $R^{32}$ are both hydrogen atoms or one is a hydrogen atom and the other a methyl group. In addition, $R^{33}$, $R^{34}$, $R^{35}$ and $R^{36}$ are each a linear or branched-chain chain alkyl group. $R^{37}$ is a hydrogen atom or an acyl group having a linear, branched-chain or ring hydrocarbon group. Examples of $R^{37}$ are an acetyl group, benzoyl group, acryloyl group, methacryloyl group and the like.

Among the polymerization inhibitors listed above, it is preferred to use phenol, 1,4-benzenediol, 4-methoxyphenol, N,N'-dialkylated-p-diphenylamine, N,N'-diphenyl-p-phenylenediamine, N,N'-di-2-naphthyl-p-phenylenediamine, N-phenyl-N'-(1,3-dimethylbutyl)-p-phenylenediamine, phenothiazine, HO-TEMPO, or BTOX; more preferably, phenol, 1,4-benzenediol, 4-methoxyphenol, phenothiazine, HO-TEMPO or BTOX; even more preferably phenol, 1,4-benzenediol, BTOX, or phenothiazine.

It is especially preferred to use phenothiazine considering the effect of suppressing polymerization. Those polymerization inhibitors may be used alone or in combination thereof. The amount of a polymerization inhibitor is set to be 0.001~2.0 mass %, preferably 0.001~1.0 mass %. When a compound containing a hydroxyl group is used as a polymerization inhibitor, its concentration is preferred to be within the concentration range of the later-described compound having a hydroxyl group.

(Reactor)

The type of a reactor used in the present embodiment is not particularly limited; for example, a batch type reactor, continuous flow stirred-tank reactor, tubular flow reactor or the like may be used. Among those, a batch type or continuous flow stirred-tank reactor is preferred, especially a batch type reactor, since a smaller change is observed in the fluid volume when a gas is generated, while it is easier to simplify the structure of the reactor. Also, it is an option to form a baffle or other structure to enhance the stirring effect in the reactor used in the present embodiment.

(Introducing Oxygen-Containing Gas)

When (meth)acrylic anhydride and a carbonate compound are reacted, an oxygen-containing gas is preferred to be introduced continuously or intermittently, more preferably continuously, into the reactor. An oxygen-containing gas may be introduced through two or more inlets of the reactor. An oxygen-containing gas may be introduced directly into the reaction mixture, or may be introduced to the gas phase. Alternatively, both methods may be used, or methods may be switched during reactions. Since reactions are facilitated or side reactions of (meth)acrylic anhydride are suppressed, an oxygen-containing gas is preferred to be directly introduced into the reaction mixture.

(Method for Introducing Raw Materials)

The method for introducing reaction materials ((meth)acrylic anhydride, carbonate compound, catalyst, carboxylic acid, solvent or the like, if applicable) is not limited particularly, and any method may be employed in any order.

(Meth)acrylic anhydride may be introduced into a reactor all at once, and then a carbonate compound as well as a catalyst, if applicable, may be added therein. When a catalyst is used, it is an option to add part or all of the (meth)acrylic anhydride by batch or continuously into a mixture that contains a carbonate compound and a catalyst. Alternatively, the methods above may be combined. In the present application, adding by batch means intermittently adding multiple times, or adding once or multiple times intermittently to the reaction mixture separately prepared in advance.

To introduce (meth)acrylic anhydride into a reactor, it is preferred to add part or all of the (meth)acrylic anhydride by batch or continuously to a mixture containing a carbonate compound and a catalyst, if applicable, from the viewpoint of suppressing side reactions. It is more preferred to continuously add part or all of the (meth)acrylic anhydride.

When (meth)acrylic anhydride is added by batch, the amount per batch may be constant or varied. However, it is preferred to reduce the amount of either of the adjacent two batches, more preferably to set a constant amount or to reduce the amounts of both of the adjacent two batches, even more preferably to reduce the amounts of both of the adjacent two batches. In addition, the intervals for adding the anhydride may be constant, increased or decreased, but it is preferred to be set constant or increased, more preferably increased.

When (meth)acrylic anhydride is continuously added, the feeding rate may be constant, increased or reduced. However, it is preferred to reduce the rate in part of the continuous feeding section, more preferably to reduce the rate in all the continuous feeding sections.

(Compound with Hydroxyl Group in Reaction Mixture)

When (meth)acrylic anhydride and a carbonate compound are reacted, the reaction may be carried out in the presence of a compound having a hydroxyl group so as to enhance reaction selectivity. In such a case, the concentration of a compound with a hydroxyl group that is present in the reaction mixture is preferred to be in a range of 0.005 mass %~10 mass % of the entire reaction material. By setting the concentration of the compound with a hydroxyl group at 0.005 mass % or greater, (meth)acrylic anhydride is converted to a (meth)acrylic acid ester at a higher selectivity rate. By setting the concentration of the compound with a hydroxyl group at 10 mass % or less, a (meth)acrylic acid ester is efficiently produced.

The concentration of a compound with a hydroxyl group is more preferred to be in a range of 0.01 mass %~5 mass %, even more preferably 0.03 mass %~3 mass %, especially preferably 0.05 mass %~2 mass %, and most preferably 0.1 mass %~2 mass %.

The compound with a hydroxyl group is not limited to a specific type, but it is preferred to contain a hydroxyl group that results when the carbonate moiety of a carbonate compound is substituted with OH. For example, when a carbonate compound is represented by formula (1) above, the compound with a hydroxyl group is preferred to be $R^{11}OH$ or $R^{12}OH$; if $R^{11}$ and $R^{12}$ are bonded, it is preferred to be HO—$R^{11}$—$R^{12}$—OH.

Examples of a compound with a hydroxyl group are phenol, ethylene glycol, propylene glycol, methanol, ethanol, propanol, and the like. Among them, phenol and ethylene glycol are preferred to suppress impurities.

To maintain the concentration of a compound with a hydroxyl group within the aforementioned preferred range, it is an option to add the compound with a hydroxyl group while monitoring its concentration in the reaction mixture using an analytical method. In a method of adding (meth) acrylic anhydride by batch or continuously, (meth)acrylic anhydride is added while the concentration of the compound with a hydroxyl group in the reaction mixture is monitored using an analytical method.

The duration to maintain the concentration of a compound with a hydroxyl group at the aforementioned preferable concentration is preferred to be part of or the entire duration after reaching the reaction temperature, more preferably 30% or longer, even more preferably 50% or longer, further more preferably 80% or longer, especially preferably 95% or longer, most preferably 100%, of the duration after reaching the reaction temperature.

(Reaction Temperature)

The temperature for carrying out the reaction of (meth) acrylic anhydride and a carbonate compound is not particularly limited, but it is preferred to be in a range of 40° C.~200° C. When the reaction temperature is set at 40° C. or higher, reaction progresses. On the other hand, when the reaction temperature is set at 200° C. or lower, decomposition or side reactions are suppressed from occurring in (meth)acrylic anhydride and the resulting (meth)acrylic acid ester.

The reaction temperature is more preferred to be in a range of 60° C.~180° C., even more preferably 80° C.~160° C., especially preferably 90° C.~140° C., and most preferably 100° C.~140° C. It is not necessary to maintain a constant reaction temperature, and the reaction temperature may vary within the preferred range.

(Reaction Time)

When a mixture containing (meth)acrylic anhydride and a carbonate compound is heated and reacted, the reaction time is not particularly limited. When a reaction is carried out at the aforementioned temperature, the reaction time is preferred to be set in a range of 0.1~150 hours, more preferably 0.3~100 hours, even more preferably 0.5~60 hours, especially preferably 1~40 hours, and most preferably 2~30 hours. When it is set to be at least 0.1 hours, the reaction progresses smoothly. In addition, when the reaction time is set to be 150 hours or less, processing costs or the like are reduced, while side reactions of (meth)acrylic anhydride and (meth)acrylic acid ester are suppressed. Accordingly, (meth) acrylic acid ester effectively is produced.

(Pressure)

The pressure during reaction is not limited to any particular level. Reaction may be carried out under reduced, normal or compressed pressure.

(Purification Process)

The (meth)acrylic acid ester produced in the present embodiment may be purified if applicable, for example, by separation, distillation, crystallization or the like. Such processes may be conducted alone, or in combination thereof. Among those, the obtained (meth)acrylic acid ester is preferred to be purified by separation and distillation.

When a (meth)acrylic acid ester is purified by a separation process, the ester is extracted by using an alkaline aqueous solution such as a sodium hydroxide solution and potassium hydroxide solution. The alkali concentration of the alkaline solution and the number of extraction times may be appropriately selected depending on reaction conditions.

Distillation is not limited to any specific method; for example, simple distillation, superfractionation, film evaporation or the like may be employed. The distillation pressure is not limited specifically. Distillation may be carried out under a reduced, normal or compressed pressure condition, but reduced pressure is preferred.

When distillation is conducted under reduced, normal or compressed pressure, it may be conducted under a nitrogen ambience or under an oxygen-containing gas ambience. However, to prevent polymerization of a (meth)acrylic acid ester, it is preferred to set the gas phase to be an oxygen-containing gas ambience, more preferably to introduce an oxygen-containing gas into a distillation apparatus, even more preferably to introduce an oxygen-containing gas directly into the solution to be used for distillation.

The conditions for crystallization are not particularly limited, and the type of the solvent, the crystallization temperature and the like may be appropriately selected depending on the type of (meth)acrylic acid ester.

Second Embodiment

In the method for manufacturing an aromatic carboxylic acid ester according to an embodiment of the present invention, a carboxylic anhydride and an aromatic carbonate are reacted in the presence of a catalyst. The catalyst is at least one type selected from among nitrogenous base-containing organic compounds, Group I metal compounds and Group II metal compounds.

In the present embodiment, a carboxylic anhydride and an aromatic carbonate are reacted using a catalyst, which is at least one type selected from among nitrogenous base-containing organic compounds, Group I metal compounds and Group II metal compounds. Accordingly, an aromatic carboxylic acid ester is produced at high yield in a short period of time from a carboxylic anhydride and an aromatic carbonate. Namely, an embodiment of the present invention provides a simplified and industrially preferable method, which is capable of efficiently producing an aromatic carboxylic acid ester. In the following, the method for manufacturing an aromatic carboxylic acid ester is described in detail according to the present embodiment.

(Carboxylic Anhydride)

The carboxylic anhydride to be used in the present embodiment indicates a carboxylic anhydride having an anhydride group (—C(=O)—O—C(=O)—) bonded to a carbon atom in the molecule. The carboxylic anhydride is not limited to a particular type, but is preferred to be represented by formula (10) below.

[chemical 16]

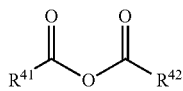

(10)

In formula (10) above, $R^{41}$ and $R^{42}$ are each independently a linear, branched-chain or ring C1~C30 alkyl group, which may have a substituent; a linear, branched-chain or ring C2~C30 alkenyl group, which may have a substituent, or a C6~C30 aryl group, which may have a substituent. $R^{41}$ and $R^{42}$ may be bonded to form a ring structure.

Examples of a carboxylic anhydride represented by formula (10) are acetic anhydride, propionic anhydride, pivalic anhydride, butyric anhydride, valeric anhydride, isovaleric anhydride, hexanoic anhydride, lauric anhydride, trifluoroacetic anhydride, trichloroacetic anhydride, angelic anhydride, tiglic anhydride, crotonic anhydride, acrylic anhydride, methacrylic anhydride, cyclohexanecarboxylic anhydride, benzoic anhydride, succinic anhydride, maleic anhydride, glutaric anhydride, phthalic anhydride, cis-1,2-cyclohexanedicarboxylic anhydride, trans-1,2-cyclohexanedicarboxylic anhydride, 3,4,5,6-tetrahydrophthalic anhydride, 2,3-naphthalene dicarboxylic anhydride, and the like.

More preferably, the carboxylic anhydride is represented by formula (11) or (12) below.

[chemical 17]

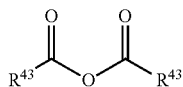

(11)

In formula (11) above, $R^{43}$ is a linear, branched-chain or ring C1~C30 alkyl group, which may have a substituent; a linear, branched-chain or ring C2~C30 alkenyl group, which may have a substituent; or a C6~C30 aryl group, which may have a substituent.

[chemical 18]

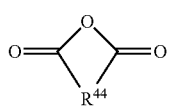

(12)

In formula (12) above, $R^{44}$ is a linear, branched-chain or ring C2~C30 alkylene group, which may have a substituent; a linear, branched-chain or ring C2~C30 alkenylene group, which may have a substituent; or a C6~C30 arylene group, which may have a substituent.

Examples of a carboxylic anhydride represented by formula (11) above are acetic anhydride, propionic anhydride, pivalic anhydride, butyric anhydride, valeric anhydride, isovaleric anhydride, hexanoic anhydride, lauric anhydride, trifluoroacetic anhydride, trichloroacetic anhydride, angelic anhydride, tiglic anhydride, crotonic anhydride, acrylic anhydride, methacrylic anhydride, cyclohexanecarboxylic anhydride, benzoic anhydride, and the like.

Examples of a carboxylic anhydride represented by formula (12) above are succinic anhydride, maleic anhydride, glutaric anhydride, phthalic anhydride, cis-1,2-cyclohexanedicarboxylic anhydride, trans-1,2-cyclohexanedicarboxylic anhydride, 3,4,5,6-tetrahydrophthalic anhydride, 2,3-naphthalene dicarboxylic anhydride and the like.

The carboxylic anhydride is more preferred to be selected from among those represented by formula (11). It is especially preferred to be acrylic anhydride or methacrylic anhydride, most preferably methacrylic anhydride, from the viewpoint of using it as polymer material. Those listed above may be used alone or in combination thereof.

(Amount of Carboxylic Anhydride)

The amount of carboxylic anhydride to be used in the present embodiment is not limited specifically, but it is preferred to be in a range of 0.1 mol~10 mol relative to 1 mol of a later-described aromatic carbonate. When the amount of carboxylic anhydride is set in a range of 0.1 mol~10 mol relative to 1 mol of an aromatic carbonate, the production amount per reaction volume is increased. Relative to 1 mol of an aromatic carbonate, the amount of carboxylic anhydride is more preferred to be in a range of 0.33 mol~5 mol, even more preferably 0.6 mol~3 mol, especially preferably 0.83 mol~1.5 mol, and most preferably 0.95 mol~1.1 mol.

(Aromatic Carbonate)

The type of aromatic carbonate to be used in the present embodiment is not limited specifically as long as it contains an aromatic group. However, the aromatic carbonate is preferred to be represented by formula (13) below.

[chemical 19]

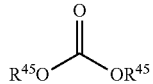

(13)

In formula (13) above, $R^{45}$ is a C6~C30 aryl group, which may have a substituent. In the present embodiment, "may have a substituent" means it may have one or more of any substituents, for example, it may have one or more of the following: ester bond, amide bond, ether bond, sulfide bond, disulfide bond, urethane bond, amino group, nitro group, cyano group, thiol group, hydroxyl group, carboxyl group, ketone group, formyl group, acetal group, thioacetal group, sulfonyl group, halogen, silicon, phosphorus, and the like.

Examples of an aromatic carbonate represented by formula (13) are diphenyl carbonate, dinaphthyl carbonate, di(4-nitrophenyl) carbonate, di(o-tolyl) carbonate, and the like.

Among them, considering the ease of obtaining the carbonate and its stability, diphenyl carbonate is preferred. Those listed above may be used alone or in combination thereof.

(Catalyst)

The catalyst used in the present embodiment is at least one type selected from among nitrogenous base-containing organic compounds, Group I metal compounds and Group II metal compounds, which may be used alone or in combination thereof. A nitrogenous base-containing organic compound means a nitrogenous base is contained in the organic compound. Nitrogenous base-containing organic compounds, Group I metal compounds and Group II metal compounds listed above in the first embodiment may also be applied in the present embodiment.
(Amount of Catalyst)

The amount of a catalyst used in the present embodiment is not particularly limited as long as an aromatic carboxylic acid ester is efficiently produced. The amount is preferred to be in a range of 0.0001 mol~0.5 mol relative to 1 mol of an aromatic carbonate. When the amount is set to be at least 0.0001 mol relative to 1 mol of the aromatic carbonate, a decrease in catalytic activity caused by impurities is effectively suppressed. When the amount is set to be no greater than 0.5 mol relative to 1 mol of the aromatic carbonate, a decrease in purity in a resulting aromatic carboxylic acid ester is effectively prevented and productivity is enhanced.

Relative to 1 mol of an aromatic carbonate, the amount of a catalyst is more preferred to be in a range of 0.0003 mol~0.3 mol, even more preferably 0.0005 mol~0.2 mol, especially preferably 0.001 mol~0.15 mol, and most preferably 0.005 mol~0.07 mol.

The catalyst used in the reaction of the present embodiment may or may not be dissolved in a reaction mixture; however, the catalyst is preferred to be dissolved. A catalyst dissolved in a reaction mixture is capable of increasing the reaction rate of producing an aromatic carboxylic acid ester.
(Carboxylic Acid)

To maintain the reaction rate, it is preferred to add a carboxylic acid when reacting a carboxylic anhydride with an aromatic carbonate. The type of carboxylic acid is preferred to be the same as that of the carboxylic anhydride. For example, it is preferred to be acrylic acid when acrylic anhydride is used, and methacrylic acid when methacrylic anhydride is used. Those carboxylic acids may be used alone or in combination thereof.
(Solvent)

A carboxylic anhydride and an aromatic carbonate may be reacted in a solvent. However, it is preferred not to use a solvent from a viewpoint of productivity. When a solvent is used, its type is not limited particularly, but it is preferred to be a C1~C25 organic compound. The solvent may contain one or more of the following: double bond, triple bond, amide bond, ether bond, sulfide bond, nitro bond, cyano bond, ketone bond, halogen, silicon, phosphorous and the like. Also, the solvent may contain a cyclic or aromatic structure. The amount of solvent is not specifically limited.

Examples of a solvent are benzene, toluene, xylene, n-hexane, cyclohexane, n-heptane, n-octane, n-nonane, n-decane, 1,4-dioxane, tetrahydrofuran, tetrahydropyran, anisole, methyl-tert-butyl ether, dibutyl ether, diphenyl ether, ethylene glycol monomethyl ether, ethylene glycol monoethyl ether, ethylene glycol mono-n-butyl ether, acetone, methyl ethyl ketone, methyl-n-butyl ketone, methyl isobutyl ketone, cyclohexanone, 2-methylcyclohexanone, dimethylformamide, dimethylacetamide and the like. They may be used alone or in combination thereof.
(Reactor)

The type of a reactor used in the present embodiment is not particularly limited; for example, a batch type reactor, continuous flow stirred-tank reactor, tubular flow reactor or the like may be used. Among those, a batch type or continuous flow stirred-tank reactor is preferred, especially a batch type reactor, since a smaller change is observed in the fluid volume when a gas is generated and it is easier to simplify the structure of the reactor. Also, it is an option to form a baffle or other structure to enhance the stirring efficiency in the reactor used in the present embodiment.

(Reaction Temperature)

The temperature for carrying out the reaction of a carboxylic anhydride and an aromatic carbonate is not particularly limited, but it is preferred to be in a range of 40° C.~200° C. When the reaction temperature is set at 40° C. or higher, reaction progresses. On the other hand, when the temperature is set at 200° C. or lower, decomposition or side reactions are suppressed from occurring in the carboxylic anhydride and the resulting aromatic carboxylic acid ester.

The reaction temperature is more preferred to be in a range of 60° C.~180° C., even more preferably 80° C.~160° C., especially preferably 90° C.~140° C., and most preferably 100° C.~140° C. It is not necessary to maintain a constant reaction temperature, and the reaction temperature may vary within the preferred range.
(Reaction Time)

When a mixture containing carboxylic anhydride and an aromatic carbonate is heated and reacted, the reaction time is not particularly limited. When reaction is carried out at the aforementioned temperature, the reaction time is preferred to be set for 0.1~150 hours, more preferably 0.3~100 hours, even more preferably 0.5~60 hours, especially preferably 1~40 hours, and most preferably 2~30 hours. When it is set at least for 0.1 hours, the reaction progresses smoothly. In addition, when reaction is carried out for 150 hours or less, processing costs or the like are reduced, while side reactions of a carboxylic anhydride and its aromatic carboxylic acid ester are suppressed. Accordingly, an aromatic carboxylic acid ester is efficiently produced.
(Pressure)

The pressure during reaction is not limited to any particular level. Reaction may be carried out under reduced, normal or compressed pressure.
(Purification Process)

The aromatic carboxylic acid ester produced in the present embodiment may be purified if applicable. An aromatic carboxylic acid ester may be purified by separation, distillation, crystallization or the like. Such processes may be conducted alone, or in combination thereof. The aromatic carboxylic acid ester is preferred to be purified by separation and distillation.

When an aromatic carboxylic acid ester is purified by a separation process, the ester is extracted by using an alkaline aqueous solution such as a sodium hydroxide solution and potassium hydroxide solution. The alkali concentration of the alkaline solution and the number of extraction times may be appropriately selected depending on reaction conditions.

The distillation method is not limited specifically; for example, simple distillation, superfractionation, film evaporation or the like may be employed. The distillation pressure is not limited to any particular level. Reaction may be carried out under reduced, normal or compressed pressure. However, reduced pressure is preferred.

The conditions for crystallization are not particularly limited, and the type of solvent, the crystallization temperature and the like may be appropriately selected depending on the type of aromatic carboxylic acid ester.

EXAMPLES

In the following, the present invention is described in further detail by referring to the examples. However, the present invention is not limited to the examples.

Examples of the First Embodiment

In the following examples, phenol, phenol methacrylate and the like were analyzed by high-speed liquid chromatography.

The following methacrylic anhydrides obtained from Sigma-Aldrich Co., LLC were used: methacrylic anhydride with a purity of 81.8 mass % (containing 0.1 mass % of methacrylic acid); methacrylic anhydride with a purity of 67.6 mass % (containing 2.4 mass % of methacrylic acid); methacrylic anhydride with a purity of 98.7 mass % (containing 1.3 mass % of methacrylic acid) obtained by distilling methacrylic anhydride with a purity of 81.8 mass %; methacrylic anhydride with a purity of 99.4 mass % (containing 0.6 mass % of methacrylic acid); methacrylic anhydride with a purity of 99.8 mass % (containing 0.2 mass % of methacrylic acid); methacrylic anhydride with a purity of 91.3 mass % (containing 1.8 mass % of methacrylic acid) obtained by distilling methacrylic anhydride with a purity of 67.6 mass %; and methacrylic anhydride with a purity of 95.2 mass % (containing 4.8 mass % of methacrylic acid).

Diphenyl carbonate with a purity of 99 mass % was obtained from Tokyo Chemical Industry Co., Ltd.

Example 1

In a 30 mmφ×200 mm test tube equipped with an air inlet, 9.52 grams (44.4 mmol) of diphenyl carbonate, 0.005 grams (0.04 mmol) of 4-dimethylaminopyridine as the catalyst, 0.008 grams of phenothiazine as the polymerization inhibitor, and 7.16 grams of methacrylic anhydride with a purity of 95.2 mass % (44.2 mmol as methacrylic anhydride) were charged. Then, methacrylic acid was added so as to set the amount of methacrylic acid in the mixture, including the methacrylic acid contained in the methacrylic anhydride, to be 0.80 grams (9.3 mmol). In an air flow of 15 mL/min., the mixture was heated to have an internal temperature of 100° C. and stirred for 3 hours. Namely, the reaction time was 3 hours. As a result, 2.71 grams (16.7 mmol) of phenyl methacrylate was produced. When calculated by formula (14) below, the yield of phenyl methacrylate in the present example was 18.8%.

[math 1]

Yield of phenyl methacrylate (%)=Produced amount of phenyl methacrylate (mol)/(Amount of methacrylic anhydride as raw material (mol)+ Amount of diphenyl carbonate as raw material (mol))×100     (14)

Examples 2~21

Reactions in the examples were conducted under the same condition as in Example 1 except for using their respective conditions shown in Table 1. The results are shown in Table 1.

Abbreviations in Table 1 denote the following: MAOMA as methacrylic anhydride, DPC as diphenyl carbonate, MAA as methacrylic acid, PHMA as phenyl methacrylate, BTOX as 4-benzoyloxy-2,2,6,6-tetramethylpiperidine-N-oxyl, DMAP as 4-dimethylaminopyridine, Mg(MAA)$_2$ as magnesium methacrylate, 4MPy as 4-methoxypyridine, 4AP as 4-aminopyridine, MIM as 1-methylimidazole, Ca(MAA)$_2$ as calcium methacrylate, and Na(MAA) as sodium methacrylate.

In Table 1, MAOMA/DPC indicates the number of moles of methacrylic anhydride relative to 1 mol of diphenyl carbonate. Catalyst/DPC indicates the number of moles of the catalyst relative to 1 mol of diphenyl carbonate. MAA/DPC indicates the number of moles of methacrylic acid relative to 1 mol of diphenyl carbonate.

From the results of Examples 1~21, it is found that a (meth)acrylic acid ester is produced by reacting (meth)acrylic anhydride and a carbonate compound in the reaction mixture. Also, from the results of Examples 1~15 and 17~21, it is found that when a nitrogenous base-containing organic compound, a Group I metal compound or a Group II metal compound is used as the catalyst, a (meth)acrylic acid ester is produced even more efficiently. Furthermore, when Examples 20 and 21 are compared, it is found that phenothiazine as a polymerization inhibitor is preferred to be present in the reaction mixture.

TABLE 1

| | Raw material for producing phenyl methacrylate | | | | | | | | MAOMA/ | catalyst/ | MAA/ | reaction condition | | Yield |
|---|---|---|---|---|---|---|---|---|---|---|---|---|---|---|
| | MAOMA | | DPC | MAA | polymerization inhibitor | | catalyst | | DPC | DPC | DPC | reaction | reaction | of |
| | mass (g) | purity (%) | (g) | (g) | type | mass (g) | type | mass (g) | (mol/mol) | (mol/mol) | (mol/mol) | temp (°C.) | time (hr.) | PHMA (%) |
| Example 1 | 7.16 | 95.2 | 9.52 | 0.80 | phenothiazine | 0.008 | DMAP | 0.005 | 0.99 | 0.001 | 0.21 | 100 | 3 | 18.8 |
| Example 2 | 7.16 | 95.2 | 9.52 | 0.80 | phenothiazine | 0.008 | DMAP | 0.056 | 0.99 | 0.010 | 0.21 | 105 | 3 | 95.2 |
| Example 3 | 7.16 | 95.2 | 9.50 | 0.80 | phenothiazine | 0.010 | DMAP | 0.054 | 1.00 | 0.010 | 0.21 | 120 | 3 | 95.5 |
| Example 4 | 7.16 | 95.2 | 9.51 | 0.80 | phenothiazine | 0.008 | DMAP | 0.0015 | 0.99 | 0.0003 | 0.21 | 130 | 3 | 21.9 |
| Example 5 | 7.16 | 95.2 | 9.51 | 0.79 | phenothiazine | 0.010 | DMAP | 0.013 | 1.00 | 0.002 | 0.21 | 130 | 3 | 94.9 |
| Example 6 | 7.16 | 95.2 | 9.51 | 0.80 | phenothiazine | 0.010 | DMAP | 0.056 | 1.00 | 0.010 | 0.21 | 130 | 3 | 96.6 |
| Example 7 | 6.14 | 95.2 | 8.09 | 0.67 | phenothiazine | 0.003 | DMAP | 0.231 | 1.00 | 0.050 | 0.20 | 130 | 3 | 98.7 |
| Example 8 | 7.60 | 81.8 | 9.52 | 0.61 | BTOX | 0.034 | Mg(MAA)$_2$ | 0.434 | 0.91 | 0.050 | 0.16 | 120 | 3 | 36.7 |
| Example 9 | 7.61 | 81.8 | 9.51 | 0.61 | BTOX | 0.034 | Mg(MAA)$_2$ | 0.434 | 0.91 | 0.050 | 0.16 | 130 | 3 | 49.1 |
| Example 10 | 7.61 | 81.8 | 9.51 | 0.62 | BTOX | 0.033 | Mg(MAA)$_2$ | 0.434 | 0.91 | 0.050 | 0.16 | 140 | 3 | 52.5 |
| Example 11 | 7.17 | 95.2 | 9.50 | 0.80 | phenothiazine | 0.010 | 4MPy | 0.050 | 1.00 | 0.010 | 0.21 | 120 | 3 | 18.6 |
| Example 12 | 7.17 | 95.2 | 9.52 | 0.80 | phenothiazine | 0.011 | 4AP | 0.044 | 1.00 | 0.011 | 0.21 | 120 | 3 | 15.6 |
| Example 13 | 7.16 | 95.2 | 9.53 | 0.79 | phenothiazine | 0.010 | MIM | 0.040 | 0.99 | 0.011 | 0.21 | 120 | 3 | 13.0 |
| Example 14 | 6.92 | 98.7 | 9.51 | 0.78 | phenothiazine | 0.029 | Ca(MAA)$_2$ | 0.467 | 1.00 | 0.050 | 0.21 | 130 | 3 | 6.6 |
| Example 15 | 6.91 | 98.7 | 9.51 | 0.78 | phenothiazine | 0.030 | Na(MAA) | 0.241 | 1.00 | 0.050 | 0.20 | 130 | 3 | 22.9 |
| Example 16 | 6.92 | 99.8 | 9.50 | 0.72 | BTOX | 0.030 | none | — | 1.01 | 0.000 | 0.19 | 130 | 3 | 2.4 |
| Example 17 | 6.90 | 98.7 | 9.51 | 0.80 | phenothiazine | 0.030 | Mg(MAA)$_2$ | 0.434 | 1.00 | 0.050 | 0.21 | 130 | 3 | 72.5 |
| Example 18 | 7.51 | 91.3 | 9.50 | 0.83 | phenothiazine | 0.034 | Mg(MAA)$_2$ | 0.436 | 1.00 | 0.051 | 0.22 | 130 | 3 | 87.5 |
| Example 19 | 10.21 | 67.6 | 9.51 | 0.68 | phenothiazine | 0.008 | Mg(MAA)$_2$ | 0.438 | 1.01 | 0.051 | 0.18 | 130 | 3 | 24.8 |

TABLE 1-continued

| | Raw material for producing phenyl methacrylate | | | | | | | | MAOMA/ DPC | catalyst/ DPC | MAA/ DPC | reaction condition | | Yield of PHMA (%) |
| | MAOMA | | | | polymerization inhibitor | | catalyst | | | | | | | |
| | mass (g) | purity (%) | DPC (g) | MAA (g) | type | mass (g) | type | mass (g) | (mol/ mol) | (mol/ mol) | (mol/ mol) | reaction temp (° C.) | reaction time (hr.) | |
|---|---|---|---|---|---|---|---|---|---|---|---|---|---|---|
| Example 20 | 7.54 | 91.3 | 9.51 | 0.82 | phenothiazine | 0.033 | Mg(MAA)$_2$ | 0.866 | 1.01 | 0.100 | 0.21 | 130 | 3 | 85.2 |
| Example 21 | 7.52 | 91.3 | 9.50 | 0.82 | BTOX | 0.034 | Mg(MAA)$_2$ | 0.867 | 1.00 | 0.101 | 0.22 | 130 | 3 | 76.3 |

Example 22

In a 30 mmϕ×200 mm test tube equipped with an air inlet, 9.51 grams (44.4 mmol) of diphenyl carbonate, 0.436 grams (2.24 mmol) of magnesium methacrylate as the catalyst, 0.034 grams of BTOX as the polymerization inhibitor, and 9.01 grams of methacrylic anhydride with a purity of 91.3 mass % (53.4 mmol as methacrylic anhydride) were charged.

Next, methacrylic acid was added so as to make the amount of methacrylic acid in the mixture, including the methacrylic acid contained in the methacrylic anhydride, to be 0.85 grams (9.9 mmol). The total amounts of raw material were 19.84 g. In an air flow of 15 mL/min., the mixture was heated to have an internal temperature of 130° C. and stirred for 3 hours. Namely, the reaction time was 3 hours. As a result, 5.90 grams (36.4 mmol) of phenyl methacrylate was produced. The yield of phenyl methacrylate to the mass of raw material (produced amount of phenyl methacrylate (g)/mass of raw material (g)) was 0.30 (g/g).

Examples 23~27

Except for the conditions shown in Table 2, the same procedures were conducted as in Example 22. The produced amount of phenyl methacrylate and the amount of phenyl methacrylate per mass of raw material in each example are shown in Table 2 as the reaction results.

Abbreviations in Table 2 denote the following: MAOMA as methacrylic anhydride, DPC as diphenyl carbonate, MAA as methacrylic acid, PHMA as phenyl methacrylate, BTOX as 4-benzoyloxy-2,2,6,6-tetramethylpiperidine-N-oxyl, and Mg(MAA)$_2$ as magnesium methacrylate.

In Table 2, MAOMA/DPC indicates the number of moles of methacrylic anhydride relative to 1 mol of diphenyl carbonate. Catalyst/DPC indicates the number of moles of the catalyst relative to 1 mol of diphenyl carbonate. MAA/DPC indicates the number of moles of methacrylic acid relative to 1 mol of diphenyl carbonate.

From the results of Examples 22~27, it is found that when the amount of methacrylic anhydride relative to 1 mol of a carbonate compound is set in a range of 0.1 mol~10 mol, the resulting production amount per reaction volume increases. It is also found that when the number of moles of a carboxylic acid at the reaction starting time is set in a range of 0.001 mol~1.5 mol relative to 1 mol of the carbonate compound, the produced amount of a (meth)acrylic acid ester per reaction volume increases.

TABLE 2

| | Raw material for producing phenyl methacrylate | | | | | | | | | | Produced | |
| | MAOMA | | | | polymerization inhibitor | catalyst | MAOMA/ DPC | catalyst/ DPC | MAA/ DPC | mass of raw | Produced amount | amount of PHMA/mass of |
| | mass (g) | purity (%) | DPC (g) | MAA (g) | BTOX (g) | Mg(MAA)$_2$ (g) | (mol/ mol) | (mol/ mol) | (mol/ mol) | material (g) | of PHMA (g) | raw material (g/g) |
|---|---|---|---|---|---|---|---|---|---|---|---|---|
| Example 22 | 9.01 | 91.3 | 9.51 | 0.85 | 0.034 | 0.436 | 1.20 | 0.051 | 0.22 | 19.84 | 5.90 | 0.30 |
| Example 23 | 7.53 | 91.3 | 9.50 | 0.83 | 0.033 | 0.437 | 1.01 | 0.051 | 0.22 | 18.33 | 8.75 | 0.48 |
| Example 24 | 7.61 | 81.8 | 9.51 | 0.61 | 0.034 | 0.434 | 0.91 | 0.050 | 0.16 | 18.20 | 6.74 | 0.37 |
| Example 25 | 6.93 | 99.8 | 9.50 | 0.01 | 0.033 | 0.437 | 1.01 | 0.051 | 0.004 | 16.91 | 4.79 | 0.28 |
| Example 26 | 7.54 | 91.3 | 9.51 | 2.34 | 0.034 | 0.439 | 1.01 | 0.051 | 0.61 | 19.86 | 8.90 | 0.45 |
| Example 27 | 6.92 | 99.8 | 9.50 | 4.92 | 0.032 | 0.436 | 1.01 | 0.051 | 1.29 | 21.80 | 7.17 | 0.33 |

Example 28

In a 50 mL three-neck round-bottom flask equipped with an air inlet, 14.26 grams (66.6 mmol) of diphenyl carbonate, 0.650 grams (3.34 mmol) of magnesium methacrylate as the catalyst, 0.098 grams of phenothiazine as the polymerization inhibitor, and 2.26 grams of methacrylic anhydride with a purity of 91.3 mass % (13.4 mmol as methacrylic anhydride) were charged. Then, methacrylic acid was added so as to set the amount of methacrylic acid in the mixture, including the methacrylic acid contained in the methacrylic anhydride, to be 1.50 grams (17.4 mmol). The mixture was heated and stirred in an air flow of 20 mL/min. until the internal temperature reached 130° C. Next, 9.00 grams of methacrylic anhydride with a purity of 91.3 mass % (53.3 mmol as methacrylic anhydride, 1.9 mmol as methacrylic acid) was continuously added at a flow rate of 0.075 g/min. in a time frame of 30~150 minutes based on the time when the internal temperature hit 130° C. having been set as zero minute. At an elapsed time of 300 minutes, the produced amount of phenyl methacrylate was 19.5 grams (120.5 mmol). When calculated by formula (14) above, the yield of phenyl methacrylate in the present example was 90.4%.

In addition, the reaction mixture was sampled at 30 minutes, 60 minutes, 120 minutes, 180 minutes, 240 minutes and 300 minutes, and the phenol concentration in the mixture was determined by liquid chromatography. The results are shown in Table 4 and FIG. 1.

Example 29

In a 50 mL three-neck round-bottom flask equipped with an air inlet, 12.36 grams (57.7 mmol) of diphenyl carbonate, 0.89 grams (10.4 mmol) of methacrylic acid, 1.124 grams (5.78 mmol) of magnesium methacrylate as the catalyst, and 0.077 grams of phenothiazine as the polymerization inhibitor were charged. Then, the mixture was heated and stirred in an air flow of 20 mL/min. until the internal temperature reached 130° C. Next, 8.97 grams of methacrylic anhydride with a purity of 98.7 mass % (57.4 mmol as methacrylic anhydride, 1.4 mmol as methacrylic acid) was continuously added at a flow rate of 0.075 g/min. in a time frame of 30~150 minutes based on the time when the internal temperature hit 130° C. having been set as zero minute. At an elapsed time of 300 minutes, the produced amount of phenyl methacrylate was 17.1 grams (105.4 mmol). When calculated by formula (14) above, the yield of phenyl methacrylate in the present example was 91.5%.

In addition, the reaction mixture was sampled at 30 minutes, 60 minutes, 120 minutes, 180 minutes, 240 minutes and 300 minutes, and the phenol concentration in the mixture was determined by liquid chromatography. The results are shown in Table 4 and FIG. 1.

Example 30

In a 50 mL three-neck round-bottom flask equipped with an air inlet, 14.26 grams (66.6 mmol) of diphenyl carbonate, 1.03 grams (12.0 mmol) of methacrylic acid, 1.297 grams (6.67 mmol) of magnesium methacrylate as the catalyst, and 0.045 grams of phenothiazine as the polymerization inhibitor were charged. The mixture was heated and stirred in an air flow of 20 mL/min. until the internal temperature reached 130° C. Then, based on the time when the internal temperature hit 130° C. having been set as zero minute, 10.35 grams of methacrylic anhydride with a purity of 98.7 mass % (66.3 mmol as methacrylic anhydride, 1.6 mmol as methacrylic acid) was continuously added at a flow rate of 0.150 g/min in the time frame of 15~42 minutes, at a flow rate of 0.050 g/min in the time frame of 42~120 minutes, at a flow rate of 0.025 g/min in the time frame of 120~180 minutes, and at a flow rate of 0.010 g/min in the time frame of 180~265 minutes. At an elapsed time of 300 minutes, the produced amount of phenyl methacrylate was 19.9 grams (122.8 mmol). When calculated by formula (14) above, the yield of phenyl methacrylate in the present example was 92.5%.

In addition, the reaction mixture was sampled at 30 minutes, 60 minutes, 120 minutes, 180 minutes, 240 minutes and 300 minutes, and the phenol concentration in the mixture was determined by liquid chromatography. The results are shown in Table 4 and FIG. 2.

Example 31

In a 50 mL three-neck round-bottom flask equipped with an air inlet, 14.29 grams (66.7 mmol) of diphenyl carbonate, 1.17 grams (13.6 mmol) of methacrylic acid, 1.300 grams (6.69 mmol) of magnesium methacrylate as the catalyst, and 0.046 grams of phenothiazine as the polymerization inhibitor were charged. The mixture was heated and stirred in an air flow of 20 mL/min. until the internal temperature reached 130° C. Then, based on the time when the internal temperature hit 130° C. having been set as zero minute, 10.30 grams of methacrylic anhydride with a purity of 98.7 mass % (66.7 mmol as methacrylic anhydride, 0.3 mmol as methacrylic acid) was continuously added at a flow rate of 0.125 g/min in the time frame of 15~45 minutes, at a flow rate of 0.052 g/min in the time frame of 45~120 minutes, at a flow rate of 0.026 g/min in the time frame of 120~205 minutes, and at a flow rate of 0.010 g/min in the time frame of 205~240 minutes. At an elapsed time of 300 minutes, the produced amount of phenyl methacrylate was 20.5 grams (126.4 mmol). When calculated by formula (14) above, the yield of phenyl methacrylate in the present example was 94.8%.

In addition, the reaction mixture was sampled at 30 minutes, 60 minutes, 120 minutes, 180 minutes, 240 minutes and 300 minutes, and the phenol concentration in the mixture was determined by liquid chromatography. The results are shown in Table 4 and FIG. 2.

Example 32

In a 30 mmφ×200 mm test tube equipped with an air inlet, 9.50 grams (44.4 mmol) of diphenyl carbonate, 7.51 grams of methacrylic anhydride with a purity of 91.3 mass % (44.5 mmol as methacrylic anhydride), 0.436 grams (2.24 mmol) of magnesium methacrylate as the catalyst, and 0.034 grams of phenothiazine as the polymerization inhibitor were charged.

Next, methacrylic acid was added so as to make the amount of methacrylic acid in the mixture, including the methacrylic acid contained in the methacrylic anhydride as raw material, to be 0.83 grams (9.6 mmol). In an air flow of 20 mL/min., the mixture was heated to have an internal temperature of 130° C. and stirred for 300 minutes. As a result, 10.9 grams (67.5 mmol) of phenyl methacrylate was produced. The yield of phenyl methacrylate calculated by formula (14) above was 76.0% in the present example.

In addition, the reaction mixture was sampled at 30 minutes, 60 minutes, 120 minutes, 180 minutes, 240 minutes and 300 minutes, and the phenol concentration in the mixture was determined by liquid chromatography. The results are shown in Table 4 and FIG. 2.

For each of Examples 28~32, the number of moles and the molar ratio of the final amount of raw material as well as the yield of phenyl methacrylate are shown in Table 3.

Abbreviations in Table 3 denote the following: MAOMA as methacrylic anhydride, DPC as diphenyl carbonate, MAA as methacrylic acid, PHMA as phenyl methacrylate, and Mg(MAA)$_2$ as magnesium methacrylate.

In Table 3, MAOMA/DPC indicates the number of moles of methacrylic anhydride relative to 1 mol of diphenyl carbonate. Catalyst/DPC indicates the number of moles of the catalyst relative to 1 mol of diphenyl carbonate. MAA/DPC indicates the number of moles of methacrylic acid relative to 1 mol of diphenyl carbonate.

From the results of Examples 28~32, it is found that part or all of the methacrylic anhydride is preferred to be added by batch or continuously in the mixture containing a carbonate compound and catalyst. Also, from the results of Examples 28~32, Table 4, FIGS. 1 and 2, it is found that 0.005 mass %~10 mass % of a compound having a hydroxyl group is preferred to be present in the reaction mixture.

TABLE 3

Raw material for producing phenyl methacrylate

|  | MAOMA (mmol) | DPC (mmol) | MAA (mmol) | catalyst Mg(MAA)$_2$ (mmol) | polymerization inhibitor phenothiazine (g) | MAOMA/ DPC (mol/mol) | catalyst/ DPC (mol/mol) | MAA/ DPC (mol/mol) | Yield of PHMA (%) |
|---|---|---|---|---|---|---|---|---|---|
| Example 28 | 66.7 | 66.6 | 19.3 | 3.34 | 0.098 | 1.00 | 0.05 | 0.29 | 90.4 |
| Example 29 | 57.4 | 57.7 | 11.8 | 5.78 | 0.077 | 0.99 | 0.10 | 0.20 | 91.5 |
| Example 30 | 66.3 | 66.6 | 13.6 | 6.67 | 0.045 | 1.00 | 0.10 | 0.20 | 92.5 |
| Example 31 | 66.7 | 66.7 | 13.9 | 6.69 | 0.046 | 1.00 | 0.10 | 0.21 | 94.8 |
| Example 32 | 44.5 | 44.4 | 9.6 | 2.24 | 0.034 | 1.00 | 0.05 | 0.22 | 76.0 |

TABLE 4

| | Phenol concentration in solution (mass %) | | | | | | Yield of PHMA (%) |
|---|---|---|---|---|---|---|---|
| | 30 min | 60 min | 120 min | 180 min | 240 min | 300 min | |
| Example 28 | 1.400 | 1.514 | 0.000 | 0.000 | 0.000 | 0.076 | 90.4 |
| Example 29 | 2.546 | 0.566 | 0.000 | 0.000 | 0.000 | 0.505 | 91.5 |
| Example 30 | 1.276 | 0.453 | 0.733 | 0.772 | 1.112 | 1.402 | 92.5 |
| Example 31 | 2.039 | 0.868 | 0.593 | 0.385 | 0.159 | 0.780 | 94.8 |
| Example 32 | 0.000 | 0.000 | 0.000 | 0.000 | 0.000 | 0.175 | 76.0 |

Examples of the Second Embodiment

In the following examples, phenol methacrylate, phenyl acetate, phenyl benzoate and the like were analyzed by high-speed liquid chromatography.

As for methacrylic anhydride, the following were used: methacrylic anhydride with a purity of 98.7 mass % (containing 1.3 mass % of methacrylic acid) obtained by distilling the methacrylic anhydride with a purity of 81.8 mass % (containing 0.1 mass % of methacrylic acid) purchased from Aldrich Co., LLC; methacrylic anhydride with a purity of 99.8 mass % (containing 0.2 mass % of methacrylic acid); and methacrylic anhydride with a purity of 95.2 mass % (containing 4.8 mass % of methacrylic acid) obtained by distilling methacrylic anhydride with a purity of 67.6 mass % purchased from Aldrich Co.

Benzoic anhydride with a purity of 99 mass % purchased from Tokyo Chemical Industry was used. Acetic anhydride with a purity of 99 mass % purchased from Wako Pure Chemical Industries, Ltd. was used. Diphenyl carbonate with a purity of 99 mass % purchased from Tokyo Chemical Industry was used.

Example 33

In a 30 mmφ×200 mm test tube equipped with an air inlet, 9.50 grams (44.4 mmol) of diphenyl carbonate, 0.054 grams (0.45 mmol) of 4-dimethylaminopyridine as the catalyst, 0.010 grams of phenothiazine as the polymerization inhibitor, and 7.16 grams of methacrylic anhydride with a purity of 95.2 mass % (44.2 mmol as methacrylic anhydride) were charged. Then, methacrylic acid was added so as to set the amount of methacrylic acid in the mixture, including the methacrylic acid contained in the methacrylic anhydride, to be 0.80 grams (9.3 mmol). In an air flow of 15 mL/min., the mixture was heated to have an internal temperature of 120° C. and stirred for 3 hours. Namely, the reaction time was 3 hours. As a result, 13.7 grams (84.6 mmol) of phenyl methacrylate was produced. When calculated by formula (15) below, the yield of phenyl methacrylate in the present example was 95.5%.

[math 2]

$$\text{Yield of phenyl methacrylate (\%)} = \text{Produced amount of phenyl methacrylate (mol)}/(\text{Amount of methacrylic anhydride as raw material (mol)} + \text{Amount of diphenyl carbonate as raw material (mol)}) \times 100 \quad (15)$$

Examples 34~45, Comparative Example 1~4

Reactions in the examples were conducted under the same condition as in Example 33 except for using their respective conditions shown in Table 5. The results are shown in Table 5.

Abbreviations in Table 5 denote the following: MAOMA as methacrylic anhydride, DPC as diphenyl carbonate, MAA as methacrylic acid, PHMA as phenyl methacrylate, BTOX as 4-benzoyloxy-2,2,6,6-tetramethylpiperidine-N-oxyl, DMAP as 4-dimethylaminopyridine, Mg(MAA)$_2$ as magnesium methacrylate, 4MPy as 4-methoxypyridine, 4AP as 4-aminopyridine, MIM as 1-methylimidazole, Ca(MAA)$_2$ as calcium methacrylate, Na(MAA) as sodium methacrylate, Ti(OBu)$_4$ as tetrabutoxytitanium, Bu$_2$SnO as dibutyltin oxide, and Sc(OTO$_3$ as scandium trifluoromethanesulfonate. No catalyst was added in Comparative Example 1.

In Table 5, MAOMA/DPC indicates the number of moles of methacrylic anhydride relative to 1 mol of diphenyl carbonate. Catalyst/DPC indicates the number of moles of the catalyst relative to 1 mol of diphenyl carbonate.

From the results in Examples 33~45 and Comparative Examples 1~4, it is found that aromatic carboxylic acid esters are efficiently produced by using at least one type of catalyst selected from among nitrogenous base-containing organic compounds, Group I metal compounds and Group II metal compounds.

TABLE 5

| | Raw material for producing phenyl methacrylate | | | | | | | MAOMA/ | catalyst/ | MAA/ | Reaction condition | | Yield |
| | MAOMA | | | | polymerization inhibitor | | catalyst | DPC | DPC | DPC | reaction | reaction | of |
| | mass (g) | purity (%) | DPC (g) | MAA (g) | type | mass (g) | type | mass (g) | (mol/mol) | (mol/mol) | (mol/mol) | temp. (° C.) | time (hr.) | PHMA (%) |
|---|---|---|---|---|---|---|---|---|---|---|---|---|---|---|
| Example 33 | 7.16 | 95.2 | 9.50 | 0.80 | phenothiazine | 0.010 | DMAP | 0.054 | 1.00 | 0.010 | 0.21 | 120 | 3 | 95.5 |
| Example 34 | 7.17 | 95.2 | 9.50 | 0.80 | phenothiazine | 0.010 | 4MPy | 0.050 | 1.00 | 0.010 | 0.21 | 120 | 3 | 18.5 |
| Example 35 | 7.17 | 95.2 | 9.52 | 0.80 | phenothiazine | 0.011 | 4AP | 0.044 | 1.00 | 0.011 | 0.21 | 120 | 3 | 15.6 |
| Example 36 | 7.16 | 95.2 | 9.53 | 0.79 | phenothiazine | 0.010 | MIM | 0.040 | 0.99 | 0.011 | 0.21 | 120 | 3 | 13.0 |
| Example 37 | 6.90 | 98.7 | 9.51 | 0.80 | phenothiazine | 0.030 | Mg(MAA)$_2$ | 0.434 | 1.00 | 0.050 | 0.21 | 130 | 3 | 72.5 |
| Example 38 | 6.92 | 98.7 | 9.51 | 0.78 | phenothiazine | 0.029 | Ca(MAA)$_2$ | 0.467 | 1.00 | 0.050 | 0.21 | 130 | 3 | 6.6 |
| Example 39 | 6.91 | 98.7 | 9.51 | 0.78 | phenothiazine | 0.030 | Na(MAA) | 0.241 | 1.00 | 0.050 | 0.20 | 130 | 3 | 22.9 |
| Example 40 | 7.16 | 95.2 | 9.52 | 0.80 | phenothiazine | 0.008 | DMAP | 0.005 | 0.99 | 0.001 | 0.21 | 100 | 3 | 18.8 |
| Example 41 | 7.16 | 95.2 | 9.52 | 0.80 | phenothiazine | 0.008 | DMAP | 0.056 | 0.99 | 0.010 | 0.21 | 105 | 3 | 95.2 |
| Example 42 | 7.16 | 95.2 | 9.51 | 0.80 | phenothiazine | 0.008 | DMAP | 0.0015 | 0.99 | 0.0003 | 0.21 | 130 | 3 | 21.9 |
| Example 43 | 7.16 | 95.2 | 9.51 | 0.79 | phenothiazine | 0.010 | DMAP | 0.013 | 1.00 | 0.002 | 0.21 | 130 | 3 | 94.9 |
| Example 44 | 7.16 | 95.2 | 9.51 | 0.80 | phenothiazine | 0.010 | DMAP | 0.056 | 1.00 | 0.010 | 0.21 | 130 | 3 | 96.6 |
| Example 45 | 6.14 | 95.2 | 8.09 | 0.67 | phenothiazine | 0.003 | DMAP | 0.231 | 1.00 | 0.050 | 0.20 | 130 | 3 | 98.7 |
| Comp. Example 1 | 6.92 | 99.8 | 9.50 | 0.72 | BTOX | 0.030 | none | — | 1.01 | 0.000 | 0.19 | 130 | 3 | 2.4 |
| Comp. Example 2 | 6.93 | 99.8 | 9.54 | 0.72 | BTOX | 0.035 | Ti(OBu)$_4$ | 0.592 | 1.01 | 0.050 | 0.19 | 130 | 3 | 0.6 |
| Comp. Example 3 | 6.92 | 99.8 | 9.50 | 0.72 | BTOX | 0.032 | Bu$_2$SnO | 0.662 | 1.01 | 0.051 | 0.19 | 130 | 3 | 2.3 |
| Comp. Example 4 | 6.91 | 98.7 | 9.51 | 0.79 | phenothiazine | 0.030 | Sc(OTf)$_2$ | 1.092 | 1.00 | 0.050 | 0.21 | 130 | 3 | 0.6 |

Example 46

In a 30 mmφ×200 mm test tube, 8.99 grams (42.0 mmol) of diphenyl carbonate, 0.015 grams (0.12 mmol) of 4-dimethylaminopyridine as the catalyst, 4.29 grams (42.0 mmol) of acetic anhydride, and 1.21 grams of anisole as the internal standard were charged. The mixture was heated to have an internal temperature of 80° C. and stirred for 3 hours. Namely, the reaction time was 3 hours. As a result, 2.55 grams (48.7 mmol) of phenyl acetate was produced. When calculated by formula (16) below, the yield of phenyl acetate in the present example was 58.0%.

[math 3]

Yield of phenyl acetate (%)=Produced amount of phenyl acetate (mol)/(Amount of acetic anhydride as raw material (mol)+Amount of diphenyl carbonate as raw material (mol))×100    (16)

Example 47

Reaction in the example was conducted under the same conditions as in Example 46 except for using the condition shown in Table 6. The result is shown in Table 6.

Abbreviations in Table 6 denote the following: Ac$_2$O as acetic anhydride, DPC as diphenyl carbonate, AcOPh as phenyl acetate, PhOMe as anisole, and DMAP as 4-dimethylaminopyridine. In Table 6, Ac$_2$O/DPC indicates the number of moles of acetic anhydride relative to 1 mol of diphenyl carbonate. Catalyst/DPC indicates the number of moles of catalyst relative to 1 mol of diphenyl carbonate.

TABLE 6

| | Raw material for producing phenyl acetate | | | | | | Ac$_2$O/ DPC | catalyst/ DPC | reaction condition | | Yield of |
| | Ac$_2$O | DPC | catalyst | | PhOMe | | | | reaction temp. | reaction time | AcOPh |
| | (g) | (g) | type | mass (g) | (g) | | (mol/mol) | (mol/mol) | (° C.) | (hr.) | (%) |
|---|---|---|---|---|---|---|---|---|---|---|---|
| Example 46 | 4.29 | 8.99 | DMAP | 0.015 | 1.21 | | 1.00 | 0.003 | 80 | 3 | 58.0 |
| Example 47 | 4.29 | 9.09 | DMAP | 0.026 | 1.01 | | 0.99 | 0.005 | 90 | 3 | >99 |

Example 48

In a 30 mmφ×200 mm test tube, 6.70 grams (31.3 mmol) of diphenyl carbonate, 7.08 grams (31.3 mmol) of benzoic anhydride, and 0.019 grams (0.16 mmol) of 4-dimethylaminopyridine as the catalyst, and 0.75 grams of anisole as the internal standard were charged. The mixture was heated to have an internal temperature of 90° C. and stirred for 3 hours. Namely, the reaction time was 3 hours. As a result, 12.4 grams (62.6 mmol) of phenyl benzoate was produced. When calculated by formula (17) below, the yield of phenyl benzoate in the present example was 80.1%.

[math 4]

Yield of phenyl benzoate (%)=Produced amount of phenyl benzoate (mol)/(Amount of benzoic anhydride as raw material (mol)+Amount of diphenyl carbonate as raw material (mol))×100    (17)

Examples 49, 50, Comparative Example 5, 6

Reactions in the examples were conducted under the same conditions as in Example 48 except for using their respective conditions shown in Table 7. Results are shown in Table 7.

Abbreviations in Table 7 denote the following: Bz$_2$O as benzoic anhydride, DPC as diphenyl carbonate, BzOPh as phenyl benzoate, PhOMe as anisole, DMAP as 4-dimethylaminopyridine, Mg(acac)$_2$.2H$_2$O as magnesium acetylacetonate dihydrate, and CF$_3$SO$_3$H as trifluoromethanesulfonic acid. No catalyst was used in Comparative Example 5. In Table 7, Bz$_2$O/DPC indicates the number of moles of benzoic anhydride relative to 1 mol of diphenyl carbonate. Catalyst/DPC indicates the number of moles of catalyst relative to 1 mol of diphenyl carbonate.

TABLE 7

|  | Raw material for producing phenyl benzoate | | | | | Reaction condition | | Yield |
|---|---|---|---|---|---|---|---|---|
|  | Bz$_2$O | DPC | catalyst | | PhOMe | Bz$_2$O/DPC | catalyst/DPC | reaction temp. | reaction time | of BzOPh |
|  | (g) | (g) | type | mass (g) | (g) | (mol/mol) | (mol/mol) | (° C.) | (hr.) | (%) |
| Example 48 | 7.08 | 6.70 | DMAP | 0.019 | 0.75 | 1.00 | 0.005 | 90 | 3 | 80.1 |
| Example 49 | 7.08 | 6.70 | DMAP | 0.042 | 0.76 | 1.00 | 0.011 | 110 | 3 | >99 |
| Example 50 | 7.08 | 6.70 | Mg(acac)$_2$•2H$_2$O | 0.089 | 0.76 | 1.00 | 0.011 | 110 | 3 | 7.0 |
| Comp. Example 5 | 7.08 | 6.70 | none | — | 0.75 | 1.00 | 0.000 | 110 | 3 | 0.0 |
| Comp. Example 6 | 7.08 | 6.70 | CF$_3$SO$_3$H | 0.052 | 0.75 | 1.00 | 0.011 | 110 | 3 | 1.3 |

The present application is based upon and claims the benefit of Japanese Patent Application Nos. 2014-121445 and 2014-121446, both filed on Jun. 12, 2014. The entire contents of these applications are incorporated herein by reference.

So far, the present invention has been described with reference to the embodiments and examples. However, the present invention is not limited to those embodiments and examples. Various modifications understandable to a person skilled in the art may be made to the structure and details of the present invention unless deviating from the scope of the present invention.

What is claimed is:

1. A method for manufacturing a (meth)acrylic acid ester, comprising:
reacting (meth)acrylic anhydride and a carbonate compound,
wherein the carbonate compound has a carbonate group (—O—C(=O)—O—) bonded to a carbon atom in the molecule, and
wherein the reaction is carried out in the presence of at least one catalyst selected from the group consisting of a primary amine compound, a secondary amine compound, a tertiary amine compound, an aromatic amine compound, an imine compound, a nitrogen-comprising heterocyclic compound of formula (5), a nitrogen-comprising heterocyclic compound of formula (6), a nitrogen-comprising heterocyclic compound of formula (7), a Group I metal compound having ionic ligands consisting of organic molecules, and a Group II metal compound having ionic ligands consisting of organic molecules:

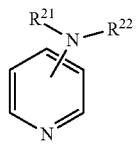

(5)

wherein, in formula (5):
the NR$^{21}$R$^{22}$ group is bonded to any of the 2-, 3-, and 4-positions of the pyridine ring,
R$^{21}$R$^{22}$ are each independently hydrogen; a linear, branched-chain or ring C1-C30 alkyl group, which may have a substituent; a linear, branched-chain or ring C2-C30 alkenyl group, which may have a substituent; or a C6-C30 aryl group, which may have a substituent, and
R$^{21}$R$^{22}$ may be bonded to form a ring structure,

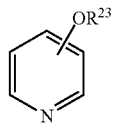

(6)

wherein, in formula (6):
the OR$^{23}$ group is bonded to any of the 2-, 3-, and 4-positions of the pyridine ring, and
R$^{23}$ is a linear, branched-chain or ring C1-C30 alkyl group, which may have a substituent; a linear, branched-chain or ring C2-C30 alkenyl group, which may have a substituent; or a C6-C30 aryl group, which may have a substituent,

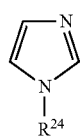

(7)

wherein, in formula (7):
R$^{24}$ is a linear, branched-chain or ring C1-C30 alkyl group, which may have a substituent; a linear, branched-chain or ring C2-C30 alkenyl group, which may have a substituent; or a C6-C30 aryl group, which may have a substituent.

2. The method for manufacturing a (meth)acrylic acid ester according to claim 1, wherein the reaction is carried out by using (meth)acrylic anhydride in a range of 0.1 mol-10 mol relative to 1 mol of the carbonate compound.

3. The method for manufacturing a (meth)acrylic acid ester according to claim 1, wherein the reaction is carried out in the presence of a carboxylic acid in a range of 0.001 mol-1.5 mol relative to 1 mol of the carbonate compound.

4. The method for manufacturing a (meth)acrylic acid ester according to claim 1, wherein the catalyst is at least one catalyst selected from the group consisting of the nitrogen-comprising heterocyclic compound of formula (5), the nitrogen-comprising heterocyclic compound of formula (6), and the nitrogen-comprising heterocyclic compound of formula (7).

5. The method for manufacturing a (meth)acrylic acid ester according to claim 1, wherein the carbonate compound is diphenyl carbonate.

6. The method for manufacturing a (meth)acrylic acid ester according to claim 1, wherein phenothiazine is present in the reaction mixture as a polymerization inhibitor.

7. The method for manufacturing a (meth)acrylic acid ester according to claim 1, wherein part or all of the (meth)acrylic anhydride is added sequentially or continuously to the mixture containing the carbonate compound.

8. The method for manufacturing a (meth)acrylic acid ester according to claim 1, wherein the reaction is carried out in the presence of a compound that contains a hydroxyl group in a range of 0.005 mass %-10 mass % relative to the reaction material.

9. The method for manufacturing a (meth)acrylic acid ester according to claim 1, wherein the reaction temperature is set to be in a range of 40° C.-200° C.

10. A method for manufacturing an aromatic carboxylic acid ester, comprising:
reacting a carboxylic anhydride and an aromatic carbonate in the presence of a catalyst,
wherein the catalyst is at least one catalyst selected from the group consisting of a primary amine compound, a secondary amine compound, a tertiary amine compound, an aromatic amine compound, an imine compound, a nitrogen-comprising heterocyclic compound of formula (5), a nitrogen-comprising heterocyclic compound of formula (6), a nitrogen-comprising heterocyclic compound of formula (7), a Group I metal compound having ionic ligands consisting of organic molecules, and a Group II metal compound having ionic ligands consisting of organic molecules:

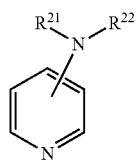

(5)

wherein, in formula (5):
the $NR^{21}R^{22}$ group is bonded to any of the 2-, 3-, and 4-positions of the pyridine ring,
$R^{21}R^{22}$ are each independently hydrogen; a linear, branched-chain or ring C1-C30 alkyl group, which may have a substituent; a linear, branched-chain or ring C2-C30 alkenyl group, which may have a substituent; or a C6-C30 aryl group, which may have a substituent, and
$R^{21}R^{22}$ may be bonded to form a ring structure,

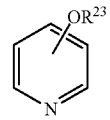

(6)

wherein, in formula (6):
the $OR^{23}$ group is bonded to any of the 2-, 3-, and 4-positions of the pyridine ring, and
$R^{23}$ is a linear, branched-chain or ring C1-C30 alkyl group, which may have a substituent; a linear, branched-chain or ring C2-C30 alkenyl group, which may have a substituent; or a C6-C30 aryl group, which may have a substituent,

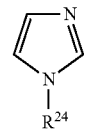

(7)

wherein, in formula (7):
$R^{24}$ is a linear, branched-chain or ring C1-C30 alkyl group, which may have a substituent; a linear, branched-chain or ring C2-C30 alkenyl group, which may have a substituent; or a C6-C30 aryl group, which may have a substituent.

11. The method for manufacturing an aromatic carboxylic acid ester according to claim 10, wherein the catalyst is at least one catalyst selected from the group consisting of the nitrogen-comprising heterocyclic compound of formula (5), the nitrogen-comprising heterocyclic compound of formula (6), and the nitrogen-comprising heterocyclic compound of formula (7).

12. The method for manufacturing an aromatic carboxylic acid ester according to claim 10, wherein the aromatic carbonate is diphenyl carbonate.

13. The method for manufacturing an aromatic carboxylic acid ester according to claim 10, wherein the carboxylic anhydride is either acrylic anhydride or methacrylic anhydride.

14. The method for manufacturing an aromatic carboxylic acid ester according to claim 10, wherein the reaction temperature is set to be in a range of 40° C.-200° C.

* * * * *